United States Patent
Becher et al.

(10) Patent No.: US 12,384,839 B2
(45) Date of Patent: *Aug. 12, 2025

(54) LIGANDS TO GM-CSF OR GM-CSF-RECEPTOR FOR USE IN LEUKEMIA IN A PATIENT HAVING UNDERGONE allo-HCT

(71) Applicant: UNIVERSITAT ZURICH, Zurich (CH)

(72) Inventors: Burkhard Becher, Maur (CH); Sonia Tugues, Zurich (CH)

(73) Assignee: UNIVERSITAT ZURICH, Zurich (CH)

( * ) Notice: Subject to any disclaimer, the term of this patent is extended or adjusted under 35 U.S.C. 154(b) by 152 days.

This patent is subject to a terminal disclaimer.

(21) Appl. No.: 18/320,162

(22) Filed: May 18, 2023

(65) Prior Publication Data

US 2023/0340100 A1    Oct. 26, 2023

Related U.S. Application Data

(63) Continuation of application No. 16/269,572, filed on Feb. 7, 2019, now Pat. No. 11,655,293.

(30) Foreign Application Priority Data

| Feb. 22, 2018 | (EP) | ................................. 18158169 |
| Aug. 17, 2018 | (EP) | ................................. 18189562 |
| Sep. 14, 2018 | (EP) | ................................. 18194549 |

(51) Int. Cl.
| A61K 39/00 | (2006.01) |
| A61P 35/02 | (2006.01) |
| A61P 37/06 | (2006.01) |
| C07K 16/24 | (2006.01) |
| C07K 16/28 | (2006.01) |

(52) U.S. Cl.
CPC ............ *C07K 16/243* (2013.01); *A61P 35/02* (2018.01); *A61P 37/06* (2018.01); *C07K 16/2866* (2013.01); *A61K 2039/505* (2013.01); *C07K 2317/21* (2013.01); *C07K 2317/24* (2013.01); *C07K 2317/76* (2013.01)

(58) Field of Classification Search
CPC .................................................. A61K 38/193
See application file for complete search history.

(56) References Cited

U.S. PATENT DOCUMENTS

| 11,655,293 | B2 | 5/2023 | Becher et al. |
| 2009/0053213 | A1 | 2/2009 | Steidl et al. |
| 2009/0130093 | A1 | 5/2009 | Cohen et al. |
| 2011/0045000 | A1 | 2/2011 | Steidl et al. |
| 2011/0165621 | A1 | 7/2011 | Dreier et al. |
| 2011/0189082 | A1 | 8/2011 | Kirchner et al. |
| 2012/0141464 | A1 | 6/2012 | Cohen et al. |
| 2012/0142611 | A1 | 6/2012 | Stumpp et al. |
| 2013/0071923 | A1 | 3/2013 | Kirchner et al. |
| 2014/0079708 | A1 | 3/2014 | Cohen et al. |
| 2015/0246969 | A1 | 9/2015 | Hartle et al. |
| 2015/0368302 | A1 | 12/2015 | Baumann |
| 2015/0376285 | A1 | 12/2015 | Cohen et al. |
| 2016/0075767 | A1 | 3/2016 | Binz |
| 2016/0250341 | A1 | 9/2016 | Steiner et al. |
| 2017/0218061 | A1 | 8/2017 | Steidl et al. |

FOREIGN PATENT DOCUMENTS

| CN | 101501070 A | 8/2009 |
| CN | 103827143 A | 5/2014 |
| EP | 1947178 | 7/2008 |
| JP | 2002-541195 A | 3/2002 |
| JP | 2007-116947 A | 5/2007 |
| JP | 2011-518857 A | 6/2011 |
| JP | 2016-117700 A | 6/2016 |
| JP | 72788296 | 5/2023 |
| JP | 72788296 B2 | 5/2023 |
| WO | WO-2009/064399 | 5/2009 |
| WO | WO-2013/004806 | 1/2013 |

OTHER PUBLICATIONS

Notice of Allowance dated Nov. 15, 2022 in respect of Mexican Patent Application No. MX/a/2020/008792.
Office Action dated Jun. 13, 2022 in respect of Mexican Patent Application No. MX/a/2020/008792.
Office Action dated Sep. 7, 2022 in respect of European Patent Application No. EP19705548.6.
Office Action dated Oct. 18, 2022 in respect of Japanese Patent Application No. 2020- 543999.
Clinical Trial: Study NCT02546284, Mar. 13, 2017, Study Page Top> [retrieved on Aug. 5, 2022] Retrieved from Internet.
International Preliminary Report on Patentability dated Sep. 3, 2020 in respect of International Patent Application PCT/EP2019/054493.
Notice of Allowance/Acceptance dated Apr. 19, 2022 in respect of Russian Patent Application No. 2020129401.
Office Action dated Nov. 22, 2021 with English translation in respect of Russian Patent Application No. 2020129401.
Office Action dated Jun. 23, 2021 in respect of Russian Application No. 2020129401.
Sakvortsova et al., Cutaneous graft-versus-host disease in a female patient a year after orthotopic liver transplantation: a case report and a review of literature, Transplantologiya (Transplantology), 1, 10, 2018, 61-67.

(Continued)

*Primary Examiner* — Prema M Mertz
(74) *Attorney, Agent, or Firm* — Mark S. Cohen; PEARL COHEN ZEDEK LATZER BARATZ LLP

(57) ABSTRACT

Described herein is the use of a non-agonist ligand, particularly an antibody, specifically binding to GM-CSF or one of CD116, CD131 and the GM-CSF receptor composed of CD116 and CD131 for use in treatment of leukemia in a patient having undergone allo-HCT or in treatment of other complications arising as a consequence of hematopoietic cell transplantation from an immunologically non-identical donor.

7 Claims, 19 Drawing Sheets

Specification includes a Sequence Listing.

(56) References Cited

OTHER PUBLICATIONS

Riott et al., Immunology, Moscow, MiR, 2000, pp. 110-111.
Singer et al., Genes and Genomes, Moscow, MIR, 1998, vol. 1, pp. 63-64.
Arellano et al., "Treatment of Relapsed Acute Leukemia after Allogeneic Transplantation: A Single Center Experience", Biology of Blood and Marrow Transplantation 2007, vol. 13, No. 1, pp. 116-123.
Bouabdallah et al., "Anti-GM-CSF Monoclonal Antibody Therapy for Refractory Acute Leukemia", Leukemia and Lymphoma 1998, vol. 30, pp. 539-549.
Cooke et al., "An Experimental Model of Idiopathic Pneumonia Syndrome After Bone Marrow Transplantation: I. The Roles of Minor H Antigens and Endotoxin", Blood 1996, vol. 8, No. 8, pp. 3230-3239.
Hartmann et al., "High-dimensional single-cell analysis reveals the immune signature of narcolepsy", J. Exp. Med. 2016, vol. 213, No. 12, pp. 2621-2633.
Hill et al., "Total Body Irradiation and Acute Graft-Versus-Host Disease: The Role of Gastrointestinal Damage and Inflammatory Cytokines", Blood 1997, vol. 90, No. 8, pp. 3204-3213.
Hill et al., "Interleukin-11 promotes T cell polarization and prevents acute graft-versus-host disease after allogeneic bone marrow transplantation", J. Clin. Invest. 1998, 102(1):115-123.
Kaplan et al., "Target Antigens Determine Graft-versus-Host Disease Phenotype", J. Immunol. 2004, 173:5467-5475.
Lerner et al., "Histopathology of Graft.-Host Reaction (GvHR) in Human Recipients of Marrow from HL-A-Matched Sibling Donors", Transplantation Proceedings 1974, vol. VI, No. 4(December), pp. 367-371.
Malkovska et al., "Tumour immunotherapy", Current Opinion in Immunology 1989, 1:883-890.
Militano et al., "Sequential administration of sargramostim (GM-CSF) and filgrastim (G-CSF) in pediatric allogeneic stem cell transplant (allosct) recipients undergoing myeloablative (MA) conditioning: Cost-effective and more rapid platelet recovery in UCB recipients", Biology of Blood and Marrow Transplantation 2006, vol. 12, Iss. 2, Supp. 1, pp. 43.
Nowicka et al., "CyTOF workflow: differential discovery in high-throughput high-dimensional cytometry datasets", F1000Research 2017, vol. 6:748.
Perfetto et al., "Seventeen-colour flow cytometry: unraveling the immune system", Nat Rev Immunol 2004, vol. 4, pp. 648-655.
Tugues et al., "Graft-versus-host disease, but not graft-versus-leukemia immunity, is mediated by GM-CSF-licensed myeloid cells", Sci. Transl. Med. 2018, vol. 10, No. 469, pp. eaat8410.
Vincke et al., "General Strategy to Humanize a Camelid Single-domain Antibody and identification of a Universal Humanized Nanobody Scaffold", J. Biol. Chem. 2009, vol. 284, No. 5, pp. 3273-3284.
International Search Report dated Mar. 12, 2019 in respect of PCT Int'l Application No. PCT/EP2019/054493.
Office Action dated Sep. 22, 2023 in respect of Chinese Patent Application No. 201980020251.7.
Notice of Allowance and Fee(s) Due dated Apr. 11, 2023 in respect of Japanese Patent Application No. 2020-543999.
Notice of Allowance dated Jan. 18, 2023 in respect of U.S. Appl. No. 16/269,572, filed Feb. 7, 2019.
Cuesta-Mateos, C. et al.; "Monoclonal Antibody Therapies for Hematological Malignancies: Not Just Lineage-Specific Targets", Frontiers in Immunology 2018, vol. 8, Art. 1936.
Office Action dated Dec. 20, 2023 in respect of U.S. Appl. No. 16/971,276.
Office Action dated Sep. 22, 2023, in respect of Chinese Patent Application No. 201980020251.7 (English translation attached).
Notice of Allowance and Fee(s) Due dated Apr. 11, 2023 in respect of Japanese Patent Application No. 2020-543999 and English translation.

1D

1E

1F

1G

Figs. 2H-2K
2H 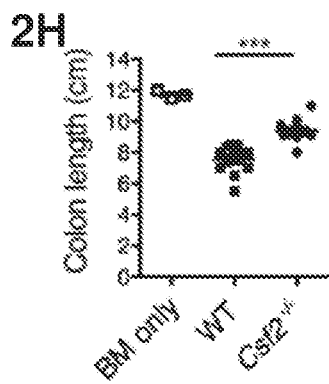
2I 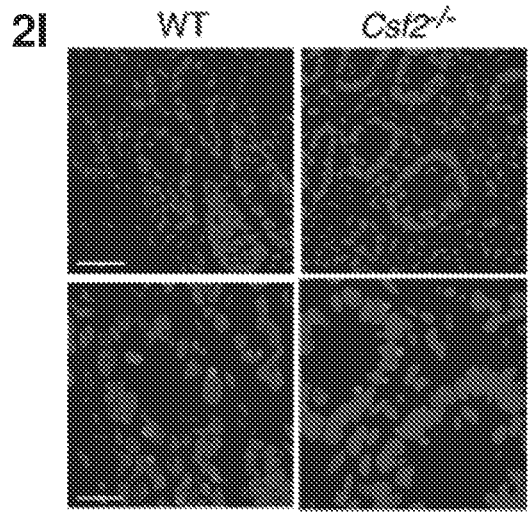 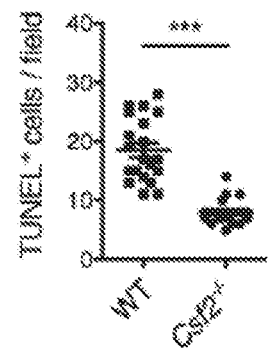
2J 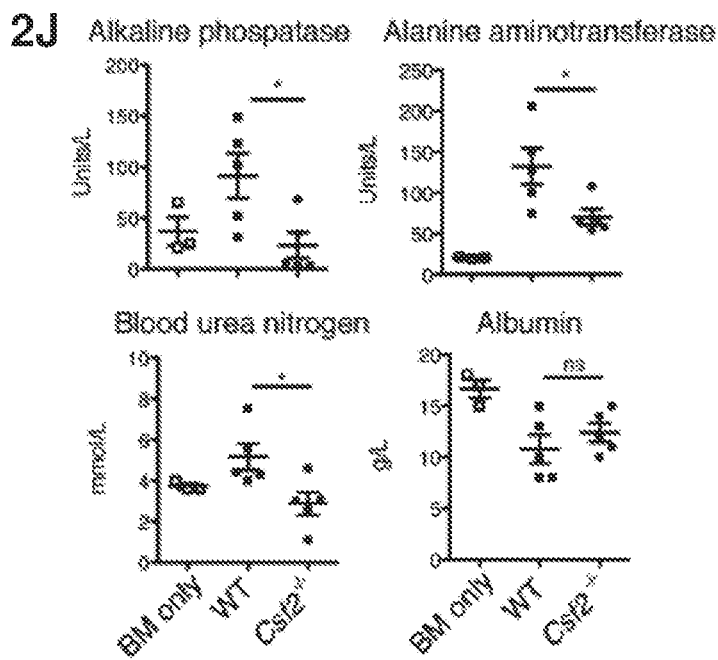
2K 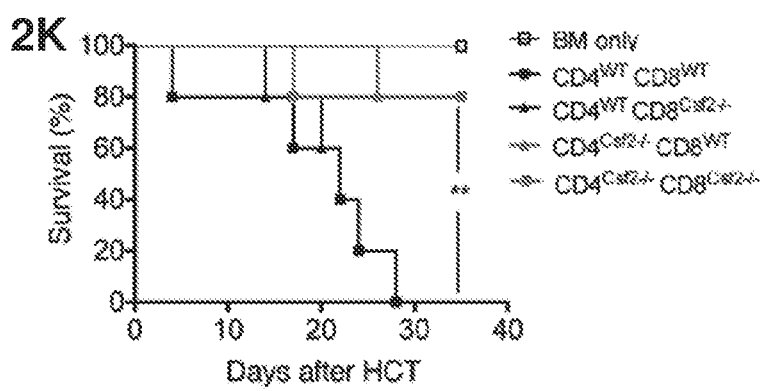

3A  3B

3C

3D

4A

4B

4C

4D

4E

4F

4G

4H

5A

5B

6A

6B

6C

6D

7A

7B

9A

9B

9C

SEQUENCE LISTING

```
Sequence total quantity: 4
SEQ ID NO: 1           moltype = DNA   length = 23
FEATURE                Location/Qualifiers
misc_feature           1..23
                       note = PCR primer
source                 1..23
                       mol_type = other DNA
                       organism = synthetic construct
SEQUENCE: 1
cactgctgct gagatgaatg aaa                                             23

SEQ ID NO: 2           moltype = DNA   length = 20
FEATURE                Location/Qualifiers
misc_feature           1..20
                       note = PCR primer
source                 1..20
                       mol_type = other DNA
                       organism = synthetic construct
SEQUENCE: 2
gtctgtaggc aggtcggctc                                                 20

SEQ ID NO: 3           moltype = DNA   length = 22
FEATURE                Location/Qualifiers
misc_feature           1..22
                       note = PCR primer
source                 1..22
                       mol_type = other DNA
                       organism = synthetic construct
SEQUENCE: 3
gaaggtgaag gtcggagtca ac                                              22

SEQ ID NO: 4           moltype = DNA   length = 22
FEATURE                Location/Qualifiers
misc_feature           1..22
                       note = PCR primer
source                 1..22
                       mol_type = other DNA
                       organism = synthetic construct
SEQUENCE: 4
tgattttgga gggatctcgc tc                                              22
```

LIGANDS TO GM-CSF OR GM-CSF-RECEPTOR FOR USE IN LEUKEMIA IN A PATIENT HAVING UNDERGONE allo-HCT

CROSS REFERENCE TO RELATED APPLICATIONS

This application is a continuation of U.S. application Ser. No. 16/269,572, filed Feb. 7, 2019, to issue as U.S. Pat. No. 11,655,293 on May 23, 2023, which is a U.S. Non-Provisional Application which claims priority to and the benefit of European Patent Application Nos. EP18158169.5, filed Feb. 22, 2018; EP18189562.4, filed Aug. 17, 2018; and EP18194549.4, filed Sep. 14, 2018, each of which is hereby incorporated by reference in its entirety.

SEQUENCE LISTING INCORPORATION

The Sequence Listing has been filed as an electronic document via Patent Center in ASCII format encoded as XML. The electronic document, created on May 17, 2023, is entitled "P-588788-USA_ST26.xml", and is 6,004 bytes in size. The Sequence Listing conforming to the rules of WIPO Standard ST.26 is hereby incorporated by reference.

FIELD

The present invention relates to a non-agonist ligand, particularly an antibody, that specifically binds to GM-CSF (CSF-2) or its receptor complex consisting of the CSF2Rβ (CD131) and CSF2Ra (CD116), for use in treatment of leukemia in a patient having undergone allo-HCT.

BACKGROUND

For patients suffering from hematological malignancies, allogeneic hematopoietic cell transplantation (allo-HCT) is a potentially-curative and life-saving intervention; however, between 40 and 60% of all patients will develop clinically-significant acute or chronic graft-versus-host disease (GvHD) which together carry a mortality rate of approximately 50%. Donor-derived T cells mediate both processes: allo-reactive T cells from the graft attack host malignant cells, producing the beneficial graft-versus-leukemia (GvL) effect; while this same allo-reactivity can be targeted towards healthy tissues (typically the skin, gut and liver), leading to GvHD. Although depleting T cells from the donor material prior to allo-HCT can prevent/reduce GvHD, accordingly this comes at the cost of decreased graft-versus-leukemia (GvL) activity and increased relapse rates. Therefore, there is an urgent need to understand how the mechanisms of GvL and GvHD can be separated at the T cell level, and modulated for clinical benefit.

Much work has attempted to define key T cell subsets and cytokines that underpin GvHD in murine models, but to date few consistent conclusions have been drawn. While GvHD was originally proposed to be a $T_H1$-mediated pathology, studies in mice showed that donor T cells deficient in the $T_H1$-cytokine IFNγ can exacerbate the disease. $T_H2$ cells can both suppress experimental GvHD, and induce GvHD affecting the liver and skin. Similarly, while there is evidence that IL-17A-producing T cells are prominent mediators of tissue damage in inflammatory diseases in general, their role in GvHD remains controversial, as in murine models IL-17 seems able to either promote or ameliorate GvHD, depending on the experimental conditions. Taken together, polarized $T_H$ cells are clearly implicated in the emergence and perpetuation of GvHD, but so far it has not been possible to identify any specific soluble mediator that has a reproducible and non-redundant function in the pathogenesis of the disease in both murine models and in humans.

Based on the above mentioned state of the art, the objective of the present invention is to provide means and methods to attenuate GvHD while maintaining the beneficial GvL effect. This objective is attained by the subject matter of the independent claims of the present specification.

SUMMARY OF THE INVENTION

A first aspect of the invention relates to a method of treating a patient suffering from graft-versus-host-disease, or a method of preventing, inhibiting, or reducing the severity of the occurrence of graft-versus-host-disease, in a patient having received an allogeneic transplant.

A second aspect of the invention relates to method of treating a patient suffering from a cancer, particularly a haematologic malignancy, and having undergone allogeneic hematopoietic stem cell transfer (allo-HCT).

The methods according to any aspect of the invention comprise interfering with the signalling of the immune cytokine GM-CSF triggering GvHD. This can be attained by inhibiting GM-CSF by ligands, particularly antibodies, interfering with GM-CSF binding to its natural receptor, or by inhibiting the signal cascade by administering non-agonist ligands to these receptors. Another possible mechanism is to suppress, transiently or for longer duration, the expression of one of GM-CSF or its receptors by nucleic acid interference (RNAi, antisense).

In particular embodiments, the invention comprises administering to the patient a non-agonist ligand, particularly an antibody, reactive to GM-CSF or to one of CD116, CD131 and the GM-CSF receptor composed of CD116 and CD131.

BRIEF DESCRIPTION OF THE FIGURES

FIG. 1A: Survival of lethally-irradiated CD45.2$^+$ BALB/c mice after allo-HCT with CD45.1$^+$ WT C57BL/6 TCD-BM alone or combined with CD45.1$^+$ WT C57BL/6 splenocytes. Data pooled from 4 individual experiments, each with n=5/group. For comparison of survival curves a Lox-rank (Mantel-Cox) test was used, ***p<0.001. FIG. 1B: Frequency of CD45.1$^+$ cells within live singlets in spleen, liver and skin at 3 and 6 days after allo-HCT. Data pooled to obtain n=10/group. FIG. 1C: Frequency of IFNγ-, GM-CSF- and IL-17A-producing CD4$^+$ and CD8$^+$ T cells within the CD45.1$^+$ population from livers of mice 3 days after allo-HCT. Representative plots are shown from a total of 3 independent experiments FIG. 1D: Frequencies of IFNγ-, GM-CSF- and IL-17A-producing CD4$^+$ and CD8$^+$ T cells within the CD45.1$^+$ populations from liver, spleen and skin 3 and 6 days after allo-HCT. Data pooled from 3 individual experiments, total n=10/group. FIG. 1E: Serum IFNγ and GM-CSF levels in mice 6 days after allo-HCT. Data pooled from 3 individual experiments, n=2-5/group. For comparison of the means an unpaired two-tailed t-test with Welch's correction was used, *p<0.05, **p<0.01. FIG. 1F: IFNγ, GM-CSF and IL-17A in supernatants from co-cultures of T cells from WT C57BU6 mice with either syngeneic (C57BU6) or allogeneic (BALB/c) splenic CD11c$^+$ DCs. Data pooled from 3 individual experiments, n=3-5/group.

For comparison of the means an unpaired two-tailed t-test with Welch's correction was used, *p<0.05, p<0.01, *p<0.001. FIG. 1G: Tritiated thymidine incorporation by T cells from C57BU6 wt, Ifng$^{-/-}$, Csf2$^{-/-}$ or Il17a$^{-/-}$ mice co-cultured with syngeneic (C57BU6) or allogeneic (BALB/c) splenic CD11c$^+$ DCs. Data pooled from 3 individual experiments, n=2-5/group. For comparison of the means one-way ANOVA with Bonferroni post-test was used. Data are displayed as mean+/−SD in FIG. 1B and as mean+/−SEM in (FIGS. 1D-1G). FIG. 1H: Frequencies of IFNγ and GM-CSF-producing CD4$_+$ and CD8$_+$ T cells within the CD45.1$_+$ populations from liver and spleen 3 and 6 days after allo-HCT. Representative data pooled from 1 of 3 experiment is shown, n=3-4/group. Abbreviations: TCD: T cell-depleted, BM: bone marrow, HCT: hematopoietic cell transfer, WT: wild type, Cpm: counts per minute.

FIGS. 2A-2K GM-CSF is crucial for acute GvHD following fully MHC-mismatched alto-HCT FIG. 2A: Survival of lethally-irradiated BALB/c mice after allo-HCT with WT C57BU6 TCD-BM alone or combined with splenocytes from C57BU6 WT Csf2$^{-/-}$, Ifng$^{-/-}$ or Il17a$^{-/-}$ mice. Data pooled from 4 individual experiments, each with n=5/group. For comparison of survival curves (WT vs other groups) a Lox-rank (Mantel-Cox) test was used, *p<0.05, p<0.01, *p<0.001. FIG. 2B: Survival of lethally-irradiated BALB/c mice after alto-HCT with WT C57BU6 TCD-BM alone or combined with T cells purified from spleens of C57BU6 WT or Csf2$^{-/-}$ mice. Data pooled from 3 individual experiments with each n=5/group. For comparison of survival curves (WT to Csf2$^{-/-}$) a Lox-rank (Mantel-Cox) test was used, ***p<0.001. FIG. 2C: Composite histo-pathological score for liver, small intestine and skin from BALB/c mice 6 days after allo-HCT. Data pooled from 3 individual experiments, n=5/group. For comparison of the means (WT vs. Csf2$^{-/-}$ an unpaired two-tailed t-test was used, *p<0.05 FIG. 2D: Representative images of haematoxylin and eosin stained sections from skin and small intestine of mice 6 days after allo-HCT with WT C57BU6 TCD-BM combined with splenocytes from either WT or Csf2$^{-/-}$ C57BU6 mice, n=4-5/group (scale bar: 100 μm). FIGS. 2E-2F: Representative images of p22phox labeling in sections from (FIG. 2E) liver and (FIG. 2F) small intestine (scale bar: 100 μm) of mice 6 days after allo-HCT with WT C57BU6 TCD-BM combined with splenocytes from either WT or Csf2$^{-/-}$ C57BU6 mice, n=4-5/group (upper panels). Quantification of mean % of total area labeled positively for p22phox per visual field. For comparison of the means (WT vs. Csf2$^{-/-}$) an unpaired two-tailed t-test was used, p<0.01. FIG. 2G: Survival of lethally-irradiated BALB/c mice following allo-HCT with WT C57BU6 TCD-BM alone or combined with splenocytes from C57BU6 WT mice. Mice were treated with PBS, isotype control antibody, or anti-GM-CSF antibody 3 times/week for the duration of the experiment, starting 2 days before HCT. Data pooled from 2 individual experiments, each with n=5/group. For comparison of survival curves (aGM-CSF vs isotype) a Lox-rank (Mantel-Cox) test was used, *p<0.001. Data are displayed as mean+/−SEM. FIG. 2H: Colon length in cm from BALB/c mice 6 days after allo-HCT, as described in a. Data pooled from 2 individual experiments. FIG. 2I: Representative images and quantification of apoptotic cells (TUNEL staining) in the colon from BALB/c mice 6 days after allo-HCT, as described in a. Data pooled from 3 individual experiments (scale bar top 50 μm, bottom 20 μm). FIG. 2J: Levels of alkaline phosphatase (AP), alanine aminotransferase (ALT), blood urea nitrogen (BUN) and albumin in serum from BALB/c mice 6 days after allo-HCT. Data is representative of 2 individual experiments, with n=3-5/group. FIG. 2K: Survival of lethally-irradiated BALB/c mice undergoing allo-HCT with WT C57BU6 TCDBM alone or combined with CD4 and CD8 T cells purified from spleens of C57BU6 WT or Csf2−/− mice (CD4WTCD8WT, CD4WTCD8Csf2−/−, CD4Csf2−/−CD8WT and CD4Csf2−/−CD8Csf2−/−). Mice treated with TCD-BM alone were used as controls. Data representative of 2 individual experiments with n=5/group. For comparison of survival curves (CD4WTCD8WT vs other groups) a Log-rank (Mantel-Cox) test was used, ns (not significant), **p<0.01. Abbreviations: TCD: T cell-depleted, BM: bone marrow, HCT: hematopoietic cell transfer, WT: wild type.

FIG. 3A: Survival of lethally-irradiated B6D2F1 mice following partially MHC-mismatched allo-HCT with WT C57BU6 TCD-BM alone or combined with splenocytes from C57BU6 WT, Csf2$^{-/-}$ or Ifng$^{-/-}$ mice. Data pooled from 5 individual experiments, each with n=5/group. For comparison of survival curves (WT vs other groups) a Lox-rank (Mantel-Cox) test was used, *p<0.05, ***p<0.001. FIG. 3B: Survival of lethally-irradiated B6D2F1 mice following allo-HCT with WT C57BU6 TCD-BM alone or combined with T cells purified from spleens of C57BU6 WT, Csf2' or Ifng' mice. Data pooled from 2 individual experiments, each with n=5/group. For comparison of survival curves (WT vs other groups) a Lox-rank (Mantel-Cox) test was used, *p<0.05, ***p<0.001. FIG. 3C: Composite histo-pathological score for liver, small intestine and skin sections from B6D2F1 mice at 11 days post allo-HCT. Data pooled from 2 individual experiments, n=5/group. For comparison of the means (WT. Csf2$^{-/-}$ and Ifng$^{-/-}$ one-way ANOVA with Bonferroni post-test was used. *p<0.05 *p<0.001. FIG. 3D: Representative images of haematoxylin and eosin stained sections from skin of mice 11 days after allo-HCT with WT C57BU6 TCD-BM combined with splenocytes from either WT, Ifng$^{-/-}$ or Csf2$^{-/-}$ C57BU6 mice, n=4-5/group (Scale bars: 100 μm). FIGS. 3E-3F: Representative images of p22phox (upper panels) and F4/80 labeling in sections from (FIG. 3E) liver and (FIG. 3F) small intestine (scale bar: 100 μm) of mice 9 days after allo-HCT with WT C57BU6 TCD-BM combined with splenocytes from C57BU6 WT or Csf2$^{-/-}$ mice, n=4-5/group. Quantification of % of total area labeled positively for p22phox or F4/80 per visual field. For comparison of the means (WT vs. Csf2$^{-/-}$) an unpaired two-tailed t-test was used, *p<0.001, **p<0.01. FIG. 3G: Serum IFNγ and GM-CSF levels in mice 9 days after allo-HCT with WT C57BU6 TCD-BM combined with splenocytes from C57BU6 WT, Ifng$^{-/-}$ or Csf2$^{-/-}$ mice. Data pooled from 2-3 individual experiments, n=4-5/group. For comparison of the means (WT vs. Ifng$^{-/-}$ or WT vs. Csf2$^{-/-}$ an unpaired two-tailed t-test with Welch's correction was used, *p<0.05, **p<0.01. Data are displayed as mean+/−SEM. FIG. 3H: Composite histopathological score for liver sections from B6D2F1 mice at 9 or 28 days post allo-HCT, as described in a. Data is representative of 2 independent experiments, n=4-6/group. Abbreviations: TCD: T cell-depleted, BM: bone marrow, HCT: hematopoietic cell transfer, WT: wild type.

FIGS. 4A-4D: Lethally-irradiated BALB/c mice were intravenously injected with A20 tumor cells expressing GFP and luciferase, at the same time as MHC-mismatched allo-HCT with WT C57BU6 TCD-BM alone or combined with T cells purified from spleens of C57BU6 WT or Csf2−/− mice. Mice treated with TCD-BM alone were used as controls. (FIG. 4A) Tumor growth was monitored by in vivo bioluminescent imaging. Images from one representative experiment of two are shown. (FIG. 4B) Signal intensity in the region of interest (ROI) was monitored over time. (FIG. 4C) Survival over time and (FIG. 4D) cause of death displayed as percentage of mice in each treatment group with lethal GvHD (grey), tumors (black) or survivors (white). Data pooled from 2 individual experiments with n=5/group. For comparison of survival curves (WT vs other groups) a Lox-rank (Mantel-Cox) test was used, ns (not significant), **p<0.01. (FIGS. 4E-4H) Lethally-irradiated BALB/c mice were intravenously injected with A20 tumor cells expressing GFP and luciferase, at the same time as MHC-mismatched allo-HCT with WT C57BU6 TCD-BM alone or combined with T cells purified from spleens of C57BU6 WT mice. Mice treated with TCD-BM alone were used as controls. Mice were treated with isotype control, or anti-GM-CSF antibody 3 times/week for the duration of the experiment, starting 2 days before HCT. (FIG. 4E) Tumor growth was monitored by in vivo bioluminescent imaging. Images from one experiment with n=6-7/group are shown. (FIG. 4F) Signal intensity in the region of interest (ROI) was monitored over time. (FIG. 4G) Survival over time and (FIG. 4H) cause of death displayed as percentage of mice in each treatment group with lethal GvHD (grey), tumors (black) or survivors (white). For comparison of survival curves (WT vs csf2$^{−/−}$) a Lox-rank (Mantel-Cox) test was used, *p<0.05. Data displayed as mean+/−SEM. Abbreviations: TCD: T cell-depleted, BM: bone marrow, HCT: hematopoietic cell transfer, WT: wild type, BLI: bioluminescent imaging, ROI: region of interest.

FIG. 5A: Relative expression of GM-CSF at the mRNA level in gastrointestinal biopsies from patients with different GvHD grades, see Table 3. For comparison of the means one-way ANOVA with Bonferroni post-test was used **p<0.01. Data are displayed as mean+/−SEM. FIG. 5B: Images of GM-CSF labeling in control and GvHD grade IV biopsies from the small intestine of allo-HCT patients, see Tables 1 & 2. Brown: anti-human GM-CSF, blue: Haematoxylin. Scale bars are 100 μm (20 μm in zoom images). Representative images of 3 individual control and patient samples are shown. FIG. 5C: Immunofluorescence staining for CD3 (pink), CD68 (green) and GM-CSF (red) of gastrointestinal biopsies from GvHD patients grade IV. A representative picture of 3 individual patient samples is shown. Nuclei are depicted in blue (DAPI) (scale bar top 50 μm, bottom 20 μm). FIG. 5D: Flow cytometric analysis of PBMCs collected from healthy donors (HD) and GvHD patients (GP), stimulated for 4 h with PMA/ionomycin. A representative FACS-Plot of cytokine expressing T cells is shown. GM-CSF, IFN, and IL-17 producing $CD4_+$ and $CD8_+$ T cells are presented as individual frequencies. n=10-9/group * P<0.05, ** P<0.01. Abbreviations: TCD: T cell-depleted, BM: bone marrow, HCT: hematopoietic cell transfer.

FIG. 6C Flow cytometric analysis of donor T cell infiltrates in recipient lymph nodes (LN), spleen, liver and skin, 2 and 5 days after allo-HCT of lethally-irradiated BALB/c mice reconstituted with WT C57BU6 TCD-BM combined with splenocytes from C57BU6 WT or Csf2−/− mice. Cells were gated on H2-db and CD45; CD4 and CD8 T cells were pre-gated on CD3. One experiment with n=4/group is shown. Data are displayed as mean+/−SEM. FIG. 6D Flow cytometric analysis of donor T cell infiltrates in recipient LN and spleen 5 days after allo-HCT of lethally-irradiated BALB/c mice reconstituted with WT C57BU6 TCD-BM combined with splenocytes from C57BU6 WT or Csf2−/− mice. Cells were gated on H2-db and CD45; CD4 and CD8 T cells. One experiment with n=4/group is shown. Data are displayed as mean+/−SEM. Abbreviations: TCD: T cell-depleted, BM: bone marrow, HCT: hematopoietic cell transfer, WT: wild type.

FIG. 7A: Flow cytometric analysis of dead cells by TO-PRO3 staining, representative plots are shown. FIG. 7B Specific lysis of A20 tumor cells by indicated T cells at target:effector ratios of 1:1, 1:20 and 1:50. Data are representative of two experiments with n=3 mice per group in each. Data are displayed as mean+/−SEM. Abbreviations: WT: wild type.

FIG. 8B Survival of lethally-irradiated Balb/c WT mice after allo-HCT with C57BU6 WT or Csf2rb−/− TCD-BM alone or combined with splenocytes from C57BL/6 WT mice. Data pooled from 2 individual experiments, each with n=5-7/group.

FIG. 9A: Survival of lethally-irradiated WT C57BU6 and Csf2rb−/− mice following MHC-mismatched allo-HCT with WT Balb/c TCD-BM alone or combined with splenocytes from Balb/c WT mice. Data pooled from 2 individual experiments, each with n=5/group. FIG. 9B: Survival of lethally-irradiated Balb/c WT mice following MHC-mismatched allo-HCT with C57BL/6 WT or and Csf2rb−/− mice TCD-BM alone or combined with splenocytes from C57BU6 WT mice. Data pooled from 2 individual experiments, each with n=5/group. For comparison of survival curves (WT vs Csf2rb−/− recipients/donors) a Log-rank (Mantel-Cox) test was used in a and b, p<0.01. FIG. 9C: Annotated t-SNE map displaying 200,000 randomly sampled cells from the bone marrow of WT C57BU6 and Csf2rb−/− mice showing STAT5 phosphorylation (black to yellow gradient) upon GM-CSF stimulation, analyzed by flow cytometric analysis. Data represent two independent experiments n=3/group. FIG. 9D: Frequencies of GM-CSF-induced pSTAT5 upregulation in monocytes and neutrophils from WT C57BU6 and Csf2rb−/− mice as shown overlayed in FIG. 9B. FIG. 9E: Flow cytometric analysis of different myeloid cell populations (DCs, neutrophils, monocytes and MDCs) after HCT. Example gating for the liver is shown. FIG. 9F: Quantification of myeloid cell populations (from FIG. 9E) in the spleen (upper row) and liver (lower row). One representative from 3 individual experiments is shown, n=4-5/group. (g) Frequency of pro-IL-1β-producing neutrophils and monocytes within the H2db+, CD45+ population from spleens of mice 6 days after allo-HCT. Representative plots are shown for neutrophils, monocytes and MDCs (gated as in e). Data represent two independent experiments n=5/group. FIG. 9H: Flow cytometric analysis of ROS (CellROX reagent) in mice 6 days after allo-HCT. Representative histograms of MFI for neutrophils, monocytes and MDCs (gated as in FIG. 9E). Data represent one experiment with n=5-7/group. For comparison of the means an unpaired two-tailed t-test was used in f-h *p<0.001, **p<0.01, *p<0.05. Data are displayed as mean+/−SEM. Abbreviations: TCD: T cell-depleted, BM: bone marrow, HCT: hematopoietic cell transfer, WT: wild type.

BRIEF DESCRIPTION OF THE DESCRIBED SEQUENCES

Figure 1A:
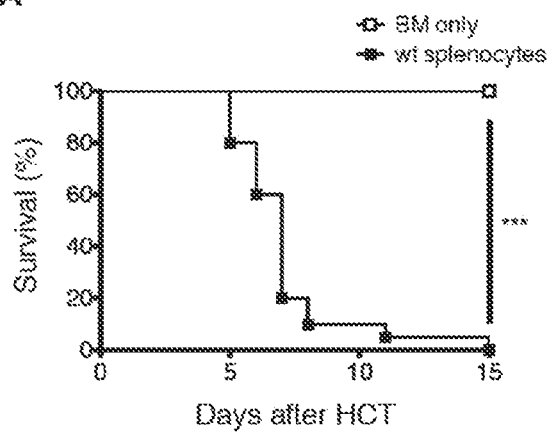
FIGS. 1A-1H Donor T cells secrete GM-CSF and IFNγ during allogeneic responses

The nucleic sequences provided herewith are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file named 95083_303_41_seglist_ST25, created Feb. 7, 2019, about 2 KB, which is incorporated by reference herein.

SEQ ID Nos: 1 and 2: forward and reverse PCR amplification primers for the CSF2 gene.

SEQ ID Nos: 3 and 4: forward and reverse PCR amplification primers for the GAPDH gene.

DETAILED DESCRIPTION OF THE INVENTION

Terms and Definitions

The term GvHD in the context of the present specification relates to graft-versus-host disease, a complication arising from transplantation of immune cells into a genetically different patient. GvHD is commonly associated with stem cell transplants, particularly in the context of therapy of hematologic malignancies, but may arise in the context of other transplantation.

The term alto-HCT in the context of the present specification relates to allogeneic hematopoietic cell transplantation.

The term GM-CSF in the context of the present specification relates to granulocyte-macrophage colony-stimulating factor (Uniprot P04141; CAS no. 83869-56-1).

The term CD116 in the context of the present specification relates to Cluster of Differentiation 116, also known as the alpha chain of the GM-CSF receptor (Uniprot P15509). The GM-CSF receptor is composed of a GM-CSF specific alpha chain (CD116) and a beta chain (CD131) that also is present in IL-3R and IL-5R interleukin receptors.

The ligand of GM-CSF or one of CD116, CD131 and the GM-CSF receptor composed of CD116 and CD131 according to the invention is able to abrogate or neutralize the signal transduction upon GM-CSF binding to its receptor.

The term CLL in the context of the present specification relates to acute chronic lymphocytic or lymphoblastic leukaemia.

The term ALL in the context of the present specification relates to acute lymphoblastic leukaemia.

The term CML in the context of the present specification relates to chronic myelogenous or myeloid leukaemia.

The term AML in the context of the present specification relates to acute myelogenous leukaemia.

The term AMoL in the context of the present specification relates to acute monocytic leukaemia.

In the context of the present specification, the term antibody is used in its meaning known in the art of cell biology and immunology; it refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region (CL). The light chain constant region is comprised of one domain, CL. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system. Similarly, the term encompasses a so-called nanobody or single domain antibody, an antibody fragment consisting of a single monomeric variable antibody domain.

The term antibody encompasses a camelid antibody, particularly a humanized camelid antibody.

The term antibody-like molecule in the context of the present specification refers to a molecule capable of specific binding to another molecule or target with high affinity/a Kd≤10E-8 mol/l. An antibody-like molecule binds to its target similarly to the specific binding of an antibody. The term antibody-like molecule encompasses a repeat protein, such as a designed ankyrin repeat protein (Molecular Partners, Zurich), an engineered antibody mimetic proteins exhibiting highly specific and high-affinity target protein binding (see US2012142611, US2016250341, US2016075767 and US2015368302, all of which are incorporated herein by reference). The term antibody-like molecule further encompasses, but is not limited to, a polypeptide derived from armadillo repeat proteins, a polypeptide derived from leucine-rich repeat proteins and a polypeptide derived from tetratricopeptide repeat proteins.

The term antibody-like molecule further encompasses a polypeptide derived from protein A domains, a polypeptide derived from fibronectin domain FN3, a polypeptide derived from consensus fibronectin domains, a polypeptide derived from lipocalins, a polypeptide derived from Zinc fingers, a polypeptide derived from Src homology domain 2 (SH2), a polypeptide derived from Src homology domain 3 (SH3), a polypeptide derived from PDZ domains, a polypeptide derived from gamma-crystallin, a polypeptide derived from ubiquitin, a polypeptide derived from a cysteine knot polypeptide and a polypeptide derived from a knottin, a polypeptide derived from a cystatin, a polypeptide derived from Sac7d, a triple helix coiled coil (also known as alphabodies), a polypeptide derived from a Kunitz domain of a Kunitz-type protease inhibitor and a polypeptide derived from a carbohydrate binding module 32-2.

The term protein A domains derived polypeptide refers to a molecule that is a derivative of protein A and is capable of specifically binding the Fc region and the Fab region of immunoglobulins.

The term armadillo repeat protein refers to a polypeptide comprising at least one armadillo repeat, wherein an armadillo repeat is characterized by a pair of alpha helices that form a hairpin structure.

In the context of the present specification, the term humanized antibody is used in its meaning known in the art of cell biology and biochemistry; it refers to an antibody originally produced by immune cells of a non-human species, the protein sequences of which have been modified to increase their similarity to antibody variants produced naturally in humans.

The term humanized camelid antibody in the context of the present specification refers to an antibody consisting of only the heavy chain or the variable domain of the heavy chain (VHH domain) and whose amino acid sequence has been modified to increase their similarity to antibodies naturally produced in humans and, thus show a reduced immunogenicity when administered to a human being. A general strategy to humanize camelid antibodies is shown in Vincke et al. "General strategy to humanize a camelid single-domain antibody and identification of a universal humanized nanobody scaffold", J Biol Chem. 2009 Jan. 30; 284(5):3273-3284, and US2011165621A1.

In the context of the present specification, the term chimeric antibody is used in its meaning known in the art of cell biology and immunology; it refers to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, cytokine, toxin, hormone, growth factor, drug, etc. For example, an antibody can be modified by replacing its constant region with a cytokine. Due to the replacement with a cytokine, the chimeric antibody can retain its specificity in recognizing the antigen while having also the function, or part thereof, of the original cytokine molecule.

In the context of the present specification, the term dissociation constant ($K_D$) is used in its meaning known in the art of chemistry and physics; it refers to an equilibrium constant that measures the propensity of a larger object to dissociate reversibly into smaller components, as when a complex falls apart into its component molecules. $K_D$ is expressed in molar units [M] and corresponds to the concentration of [Ab] at which the binding sites of [Ag] are half occupied. In other words the concentration of unbound [Ab] equals the concentration of the [AbAg] complex. The dissociation constant can be calculated according to the following formula:

$$K_D = \frac{[Ab] * [Ag]}{[AbAg]}$$

[Ab]: concentration of antibody; [Ag]: concentration of antigen; [AbAg]: concentration of antibody antigen complex In the context of the present specification, the terms off-rate (Koff; [1/sec]) and on-rate (Kon; [1/sec*M]) are used in their meaning known in the art of chemistry and physics; they refer to a rate constant that measures the dissociation (Koff) or association (Kon) of 5 an antibody with its target antigen. Koff and Kon can be experimentally determined using methods well established in the art. A method for determining the Koff and Kon of an antibody employs surface plasmon resonance. This is the principle behind biosensor systems such as the Biacore® or the ProteOn® system. They can also be used to determine the dissociation constant KD by using the following formula:

$$K_D = \frac{[K_{off}]}{[K_{on}]}$$

As used herein, the term "treating" or "treatment" of any disease or disorder (e.g. cancer or graft versus host disease) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

In the context of the present specification, the term aptamer refers to an oligonucleotide or peptide capable of specifically binding to another molecule or target with high affinity having a Kd≤10E-8 mol/l. An aptamer binds to its target similarly to the specific binding of an antibody. The term aptamer encompasses RNA or DNA molecules, nucleic acid analogues or peptide molecules. An aptamer may also be coupled to a self-cleaving RNA molecule, so-called ribozyme. Methods are known for obtaining aptamers de-novo; these include the so-called "selex" approach and other methods based on evolution of specific binders from a random selection.

Using murine models of fully- and partially-MHC-mismatched HCT, the inventors showed that GM-CSF (Csf-2), a cytokine with an emerging role across a range of inflammatory disorders, is abundantly produced by donor T cells early after transfer. When donor T cells lacked GM-CSF, GvHD was significantly ameliorated. Importantly and surprisingly, the absence of GM-CSF did not affect donor T cells' ability to control tumor growth in mice (the GvL effect), and this control was achieved without the emergence of GvHD even in the context of full MHC-mismatch. The inventors also uncovered high levels of GM-CSF in gastrointestinal biopsies from GvHD patients, consistent with a parallel role in the human condition. Therefore, the inventors propose GM-CSF as a novel therapeutic target to attenuate GvHD while maintaining GvL in patients receiving allo-HCT.

While the use of anti-GMCSF or anti-GMCSFR antibodies has been proposed in the context of GvHD, the data presented here for the first time show that GvHD can be treated or inhibited without effecting the therapeutic benefit of an allogenic transplant, and that there is a clinical rationale for employing the ligands of the invention for allowing the body to mount a graft-versus-leukemia response while suppressing GvHD (phagocyte mediated). This will permit including patients for alto-HCT, who at present are not scheduled for alto-HCT due to the risk posed by GvHD, and may further allow to limit the use of immunosuppressants after allo-HCT.

A first aspect of the invention relates a non-agonist ligand specifically binding to GM-CSF or to one of CD116, CD131 and the GM-CSF receptor composed of CD116 and CD131 for use in treatment of leukemia in a patient having undergone allogeneic hematopoietic stem cell transfer (alto-HCT). In other words, the ligand is used for treatment of leukemia subsequent to allgeneic hematopoietic stem cell transfer.

The non-agonist ligand of the invention abrogates the biological signal exerted by GM-CSF on its receptor, leading to the downstream effects of the interaction of GM-CSF. Accordingly, it will be appreciated that the methods described herein can be used to inhibit or reduce the severity of GvHD in the context of any allogenic transplant in which GvHD can occur, but without significantly diminishing the beneficial effect of the allogeneic transplant. In particular embodiments, described herein are methods for treatment of a haematologic malignancy including leukaemia, lymphoma, or a multiple myeloma by administering to a patient the described non-agonist ligand concurrently with or following provision of an alto-HCT treatment for the malignancy. In other embodiments, the methods for inhibiting or reducing the severity of GvHD enables provision of an allogenic transplant in which the risk exists for induction of GvHD by sufficient GM-CSF producing or inducing cells transplanted along with the allotransplant. Liver transplantation is one non-limiting example of such a transplant.

In certain embodiments, the non-agonist anti-GM-CSF, anti-CD116, anti-CD131 or anti-GM-CSF receptor ligand is an antibody, antibody fragment, an antibody-like molecule, aptamer or a protein A domains derived polypeptide. While the use of antibodies, particular monoclonal antibodies, is common for therapeutic uses in human patients, and indeed, GM-CSF-specific antibodies and CD116-specific antibodies have been developed for other therapeutic purposes, the skilled person understands that other modalities such as DARPINs, aptamers, or antibody-derived molecules can be employed to serve essentially the same purpose.

In some embodiments, the non-agonist anti-GM-CSF, anti-CD116, anti-CD131 or anti-GM-CSF receptor polypeptide ligand is an immunoglobulin consisting of two heavy chains and two light chains. In some embodiments, the non-agonist anti-GM-CSF, anti-CD116, anti-CD131 or anti-GM-CSF receptor polypeptide ligand is a single domain antibody, consisting of an isolated variable domain from a heavy or light chain. In some embodiments, the non-agonist anti-GM-CSF, anti-CD116, anti-CD131 or anti-GM-CSF receptor polypeptide ligand is a heavy-chain antibody consisting of only heavy chains such as antibodies found in camelids.

In certain embodiments, the non-agonist anti-GM-CSF, anti-CD116, anti-CD131 or anti-GM-CSF receptor polypeptide ligand is an antibody fragment. In certain embodiments, the non-agonist anti-GM-CSF, anti-CD116, anti-CD131 or anti-GM-CSF receptor polypeptide ligand is a Fab fragment, i.e. the antigen-binding fragment of an antibody, or a single-chain variable fragment, i.e. a fusion protein of the variable region of heavy and the light chain of an antibody connected by a peptide linker.

The effect of treatment with an antibody to GM-CSF in a mouse model of a post-allo-HCT leukemia treatment is shown in FIG. 4.

In certain embodiments, the ligand is a monoclonal antibody. In certain embodiments, the ligand is a human antibody.

In certain embodiments, the ligand for use in a method of treatment of a haematologic malignancy, such as leukemia, in a patient having undergone allogeneic hematopoietic stem cell transfer (allo-HCT) is a humanized antibody. In certain embodiments, the ligand is a chimeric antibody.

In certain embodiments, the ligand for use in a method of treatment of a haematologic malignancy, such as leukemia in a patient having undergone alto-HCT is Mavrilimumab (CAS No. 1085337-57-0).

In certain embodiments, the ligand for use in a method of treatment of a haematologic malignancy, such as leukemia in a patient having undergone alto-HCT is Namilumab (CAS No. 1206681-39-1).

In certain embodiments, the ligand for use in a method of treatment of a haematologic malignancy, such as leukemia in a patient having undergone alto-HCT is Lenzilumab (CAS No. 1229575-09-0). In certain embodiments, the ligand for use in a method of treatment of a haematologic malignancy, such as leukemia in a patient having undergone alto-HCT is Otilimab (MOR103 or GSK-3196165; CAS NO. 1638332-55-4). In certain embodiments, the ligand for use in a method of treatment of a haematologic malignancy, such as leukemia in a patient having undergone alto-HCT is Gimsilumab (MORAb-022; CAS No. 1648796-29-5).

It will be appreciated that in particular embodiments, an antibody, such as mavrilimumab, namilumab, lenzilumab, otilimab, or gimsilumab can be used in methods for provision of an allogenic transplant, in which the development of GvHD is inhibited or its severity is reduced.

In certain embodiments, the ligand for use in a method of treatment of leukemia in a patient having undergone allo-HCT is characterized by a $K_D$ of smaller than (<) $10^{-7}$, particularly $K_D<10^{-8}$, more particularly $K_D<10^{-9}$.

A second aspect of the invention relates to a nucleic acid molecule encoding the ligand as specified in the first aspect of the invention or any of its specific embodiments, for use in treatment of leukemia in a patient having undergone alto-HCT.

In certain embodiments, the nucleic acid molecule for use in treatment of a haematologic malignancy, such as leukemia in a patient having undergone allo-HCT is a single stranded or double stranded DNA molecule or an single stranded or double stranded RNA molecule.

In certain embodiments, the nucleic acid molecule for use in treatment of leukemia, or other malignancy, in a patient having undergone allo-HCT according to the invention is a nucleic acid expression construct comprising the nucleic acid sequence specified above under control of a promoter operable in a mammalian cell.

In certain embodiments, the nucleic acid molecule for use in treatment of a haematologic malignancy, such as leukemia in a patient having undergone allo-HCT is an expression construct selected from a DNA plasmid, a double stranded linear DNA, a single stranded RNA and a virus, particularly a lentivirus, a herpesvirus, an adenovirus or an adeno-associated virus.

The nucleic acid expression construct is used to introduce a specific gene into a target cell, and can commandeer the cell's mechanism for protein synthesis to produce the protein encoded by the gene. The nucleic acid expression construct is engineered to contain regulatory sequences that act as promoter regions and optionally also sequences that act as enhancer regions and lead to efficient transcription of the gene carried on the expression construct.

Nucleic acid expression vectors for use in the described methods are common in the art. Illustrative vectors for expression of mammalian proteins include those available, inter alia, from Promega Corp (Madison, WI) and Thermo Fisher Scientific, Inc. (Waltham, MA).

In another embodiment, as an alternative to administering a non-agonist ligand, the described methods of treatment include inhibiting the expression of GM-CSF, its receptor (CD116 and CD131), or an individual subunit of the GM-CSF receptor (CD116 and/or CD131). In such methods, a nucleic acid capable of inhibiting the expression GM-CSF or its receptor peptides is provided to a patient in need thereof (e.g. following or during allo-HCT). In particular embodiments, the targeting nucleic acid can be an antisense DNA, siRNA, or the like. Methods of determining suitable target and targeting sequences are known to the art.

An alternative of the above aspects of the invention relates to a pharmaceutical composition for use in treatment of a haematologic malignancy, such as leukemia in a patient having undergone allo-HCT. The composition comprises the non-agonist ligand specifically binding to GM-CSF or one of CD116, CD131 and the GM-CSF receptor composed of CD116 and CD131 or the nucleic acid expression construct encoding same, and a pharmaceutically acceptable carrier, particularly formulated as an administration form for parenteral administration, more particularly for intravenous administration.

Antibodies against GM-CSF and against one of CD116, CD131 and the GM-CSF receptor composed of CD116 and CD131 are known in the art. Monoclonal antibodies specific to GM-CSF have been developed and tested clinically for efficacy in rheumatoid arthritis. Non-limiting examples of antibodies for practicing the current invention include CD116/131 antibodies disclosed in US2014079708, US2012141464, US2009130093, US2014079708 and US2015376285, all to Cohen et al. (Mavrilimumab), incorporated herein by reference.

Another non-limiting example is the GM-CSF antibody (Otilimab) disclosed in US2015246969 to Haertle et al., and the antibodies of US2011189082 and US2013071923 to Kirchner et al., all of which are incorporated herein by reference.

Another non-limiting example is the GM-CSF antibody disclosed in US2009053213, US2011045000, US2017218061 to Steidl et al., all of which are incorporated herein by reference.

Another antibody against GM-CSF is being developed for the use in rheumatoid arthritis by Takeda under the name Namilumab.

Another antibody against GM-CSF is undergoing a clinical trial in subjects with previously treated chronic myelomonocytic leukemia (CMML) under the name Lenzilumab (CAS No. 1229575-09-0).

Similarly within the scope of the present invention is a method of treating a haematologic malignancy, such as leukemia in a patient having undergone allo-HCT, comprising administering to the patient a non-agonist ligand, particularly an antibody, specifically binding to GM-CSF or one of CD116, CD131 and the GM-CSF receptor composed of CD116 and CD131 according to the above description.

Similarly, a dosage form for the prevention or treatment of leukemia in a patient having undergone allo-HCT is provided, comprising a ligand or nucleic acid construct according to one of the above aspects of the invention.

Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Wherever alternatives for single separable features are laid out herein as "embodiments", it is to be understood that such alternatives may be combined freely to form discrete embodiments of the invention disclosed herein.

The invention is further described exemplarily by the following items:

Item 1: A non-agonist ligand specifically binding to
GM-CSF or
one of CD116, CD131 and the GM-CSF receptor composed of CD116 and CD131,
for use in treatment of GvHD.

Item 2: The ligand for use in treatment of GvHD according to item 1, wherein the ligand is an antibody, antibody fragment, aptamer or antibody-like molecule.

Item 3: The ligand, according to item 1 or 2 for use in treatment of GvHD, wherein the ligand is a human antibody or a humanized antibody.

Item 4: The ligand according to any one of the preceding items for use in treatment of GvHD, selected from Mavrilimumab, Namilumab, Lenzilumab, MOR103, and MORAb-022.

Item 5: The ligand according to any one of the preceding items for use in treatment of GvHD, wherein the binding of the ligand to GM-CSF or one of CD116, CD131 and the GM-CSF receptor composed of CD116 and CD131 is characterized by a $K_D$ of smaller than (<) $10^{-7}$, particularly $K_D<10^{-8}$, more particularly $K_D<10^{-9}$.

Item 6: A nucleic acid molecule encoding the ligand according to any one of the preceding items 1 to 4 for use in treatment of GvHD.

Item 7: The nucleic acid molecule for use in treatment of GvHD according to item 6, wherein the nucleic acid molecule is a DNA molecule or an RNA molecule.

Item 8: A nucleic acid expression construct comprising the nucleic acid sequence of item 5 or 7 for use in treatment of GvHD.

Item 9: The nucleic acid expression construct for use in treatment of GvHD according to item 8, wherein the expression construct is selected from a DNA plasmid, a double stranded linear DNA, a single stranded RNA and a virus, particularly a lentivirus, a herpesvirus, an adenovirus or an adeno-associated virus.

Item 10: The ligand according to any one of the preceding items 1 to 5 or the nucleic acid molecule according to items 6 or 7, or the nucleic acid expression construct according to item 8 or 9, for use in treatment of complications arising as a consequence of allo-HCT.

The invention is further illustrated by the following examples and figures, from which further embodiments and advantages can be drawn. These examples are meant to illustrate the invention but not to limit its scope.

EXAMPLES

Material and Methods

Study Design

The study was initiated to determine whether certain T cell-derived cytokines could separate GvHD from GvL and so may represent promising novel therapeutic targets for the treatment of hematologic malignancies. To achieve this aim, we used two different experimental models of GvHD, an experimental model of GvL and human subjects. For animal studies, 8- to 12-week-old mice were used. All animal experiments were approved by local authorities (Swiss Cantonal Veterinary Office) and performed under the appropriate experimental licenses (76/2012 and 052/2015). Animals were assigned randomly into the experimental groups and in-life clinical score was performed in a blinded fashion as well as image analysis processing on organ sections. Sample size and disease end time points were selected on the basis of previous studies. Flow cytometry, histopathological analysis, mixed lymphocyte reactions (MLRs), killing assays and cytokine analysis were performed to characterize the GvHD/GvL target organs. The effects of the specific GM-CSF blocking antibody on clinical score were assessed by investigators who were blind for the treatment.

To perform reliable statistical analysis, at least three independent experiments were conducted for each data shown in the manuscript, unless differently indicated in the figure legends. All human samples were collected after approval by the ethics committee of the Albert-Ludwigs University Freiburg, Germany (Protocol number: 267/11) following written informed consent. We performed immunohistochemistry and quantitative RT-PCR on the gut biopsies, and multiparameter flow cytometry on the PBMCs.

Mice and In vivo manipulations. Mice were kept in-house in individually ventilated cages under specific pathogen-free conditions. WT C57BU6, BALB/c and B6D2F1 mice were purchased from Janvier Laboratories, France. Congenic C57BU6 CD45.1 mice were bred in-house. Ifng$^{-/-}$ mice were obtained from Jackson Laboratories; Csf2$^{-/-}$ mice were provided by Jeffrey Whitsett and further backcrossed to C57BU6 using speedy congenics. Il17a$^{-/-}$ mice were provided by Y. Iwakura. All animal experiments were approved by local authorities (Swiss Cantonal Veterinary Office) and performed under the appropriate experimental licenses (76/2012 and 052/2015). 7-12 week old female mice were used for experiments throughout.

Induction of GvHD: Single cell suspensions from spleen and BM of donor C57BU6 or BALB/c mice were prepared as described below (under "Lymphocyte isolation"). For T cell depletion of BM, cells were incubated at 25×10$^6$/ml in RMPI complete (RPM 1640 with 10% FCS, 1% Penicillin/Streptomycin, 2 mM L-Glutamine and 0.5 mM β-mercaptoethanol) with αCD90.2-Biotin (1:100, eBioscience) for 30 minutes at 4° C. with agitation. Subsequently, after a washing step with cold MACS buffer (PBS with 0.5% BSA and 2 mM EDTA), cells were resuspended at 100×10$^6$ cells/ml in MACS buffer and incubated with anti-Biotin beads (1:5, Miltenyi) or Streptavidin beads (1:10, Miltenyi) for 20 minutes at 4° C. with agitation. After washing with MACS buffer, cells were separated using the AutoMACS Pro, Miltenyi Biotech and the 'depletes' program. The negative fraction was collected and cell numbers were determined using a counting chamber. Depletion efficiency was analyzed by flow cytometry. T cell frequencies in BM were reduced from 1-3% to 0.055+/−0.022%. For isolation of untouched T cells from splenocytes the Pan T cell isolation kit (II) from Miltenyi was used according to the manufacturers protocol. Cells were separated using the AutoMACS Pro, Miltenyi Biotech and the 'deplete' program. The negative fraction was collected and cell numbers were determined using a counting chamber. Enrichment efficiency was analyzed by flow cytometry and T cell purity was routinely 95.2+/−2.16%. CD4 and CD8 T cells were separated using the MojoSort Mouse CD4 T cell isolation and the MojoSort Mouse CD8 T cell isolation kits according to the manufacturer's instruction (Biolegend).

Recipient BALB/c or B6D2F1 mice were lethally-irradiated under specific pathogen free conditions in filter-cages with a split-dose of 850 (BALB/c), 1200 (B6D2F1) or 1100 (C57BU6) rad, separated by at least 5 hours. Recipients were injected i.v. with 5×10$^6$ BM cells and 0.1 10×10$^6$ splenocytes or 6-7.5*10$^6$ T cells per C57BU6 or B6D2F1 mouse. Recipients were injected i.v. with 7×10$^6$ BM cells and 20×10$^6$ splenocytes/BALB/c mouse. Mice were treated with 0.1% Borgal (Intervet) in drinking water for three weeks to prevent bacterial infections. Mice were also scored daily for GvHD symptoms, adapted from (Cooke, K. R. et al. An experimental model of idiopathic pneumonia syndrome after bone marrow transplantation: I. The roles of minor H antigens and endotoxin. *Blood* 88, 3230-3239 (1996)), and shown in Supplementary Table 4. Investigators were blinded to group allocation when scoring GvHD. Reference weight was measured on day 0, prior to injection of graft cells. For blocking of GM-CSF, mice were treated with PBS, 300 µg isotype control (2A3) or 300 µg anti-GM-CSF antibody (MP1) (BioXCell) 3 times/week starting 2 days before HCT.

Induction of GvL: The A20-Luciferase$^+$ GFP$^+$ B cell lymphoma cell line (A20-luc-gfp, kindly provided by Emma Svensson, Department of Immunology, Genetics and Pathology, Uppsala University, Sweden) was generated on a BALB/c background by transduction of A20 (ATCC) with a lentivirus encoding CMV-GFP-(T2A)-Luc. WEHI-3-luciferase+ cells were donated by R. Zeiser. On the day of HCT, 2.5×105 A20 cells, 5×105 A20 cells or 1×105 WEHI-3 cells per mouse were injected intravenously, alongside 5×106 WT C57BU6 BM cells, either alone or with 1×105 purified splenic T cells/mouse from either WT or Csf2−/− C57BU6 mice. On the day of HCT, 2.5×10$^5$ A20 cells per mouse were injected intravenously, alongside 5×10$^6$ WT C57BU6 BM cells, either alone or with 1×10$^5$ purified splenic T cells/mouse from either WT or Csf2$^{-/-}$ C57BU6 mice. Tumor progression was monitored by bioluminescence imaging (BLI): mice were injected intraperitoneally with 150 mg/kg of D-luciferin (Promega) in PBS ten minutes prior to imaging using the Xenogen IVIS 200 preclinical in vivo imaging system (PerkinElmer, Waltham, MA); exposure times 1-120 s, binning 2-8, FOV 15 cm, f/stop 1, no filter. Mice were anesthetized with isoflurane (2% vaporized in O2) prior to and during imaging. Total photon flux (photons/sec) was measured from a fixed region-of-interest (ROI) over the full body using Living Image software (PerkinElmer). Pictures were always taken for each cage and have been cropped when different groups of mice were mixed within the same cage. Tumor and GvHD mortality were distinguished by BLI signal intensity (ROI>1*10$^7$ for tumor incidence), hind-limb paralysis (indicating tumor development) and clinical manifestations of GvHD (at least a grade 2 in two of the individual GvHD criteria). For blocking of GM-CSF, mice were treated with 300 µg isotype control (2A3) or 300 µg anti-GM-CSF antibody (MP1) (BioXCell) 3 times/week starting 2 days before HCT. From week 3 on the antibody dose was reduced to 150 µg.

Lymphocyte Isolation. Mice were euthanized using $CO_2$ inhalation and perfused with 40 ml cold PBS. Unless otherwise specified below, organs were harvested, cut into small pieces and incubated with Collagenase at 37° C., followed by mechanical disruption by repeated passage through a 20 gauge needle. Red blood cell lysis was performed. The resulting cell suspension was then filtered through a 70 µm cell strainer and used for further procedures.

Spleen: For the isolation of myeloid cells, organ pieces were incubated in 2 ml of Collagenase D (0.4 mg/ml, Roche) and 0.1 mg/ml DNase I (Sigma) in RPMI for 30 minutes at 37° C. For isolation of T cells, spleens were homogenized by mechanical disruption and filtered through a 70 µm cell strainer. BM: Femurs, tibias and pelvis were flushed with PBS to obtain BM stem cells. Liver: organ pieces were incubated in 1.6 mg/ml Collagenase Type IV (from *Clostridium histolyticum*, Sigma) in HBSS containing 10% FCS for approximately 45 minutes at 37° C. Cells were resuspended in 10 ml Percoll, (continuous gradient, 27%, GE) and centrifuged for 30 minutes at 1700 rpm at RT. Fat and supernatant was removed and the pellet was subjected to red blood cell lysis. Skin: organ pieces were incubated in 1 mg/ml Collagenase Type IV (from *Clostridium histolyticum*. Sigma) and 0.1 mg/ml DNase I (Sigma) in RPMI for 1.5-2 hours at 37° C. Small intestine: organs were separated from the mesenteric fat before lumina) mucus was removed mechanically; organs were then incubated in calcium- and magnesium-free HBSS containing 2% FCS, 1 mM DTT and 1.35 mM EDTA for 15 min at 37° C. After further incubation in HBSS complemented with EDTA for 30 min at 37° C. the colons were cut and digested using 0.4 mg/ml collagenase IV (Sigma Aldrich) for 45 min at 37° C. The samples were then homogenized using a syringe with an 18 gauge needle and filtered through a 70 µm cell strainer.

Flow cytometry. Flow cytometric analysis was performed following standard methods, reviewed in (Perfetto, S. P., Chattopadhyay, P. K. & Roederer, M. Seventeen-colour flow cytometry: unravelling the immune system. *Nat Rev Immunol* 4, 648-655 (2004)). For all fluorochrome-conjugated antibodies optimal concentrations were determined using titration experiments. Antibody clones specific for mouse CD4 (GK1.5), CD8 (53-6.7), CD3 (17A2), CD45 (30F11), CD45.1 (A20), CD45.1 (104), CD44 (IM7), CD62L (MEL-14), CD69 (H1.2F3), MHC class I H2-D$^d$ (34-2-12) and H2-db (KH95), GM-CSF (MP1-22E9), IFNγ (TC11-18H10), IL-17A (XMG1.2) and FoxP3 (FJK-16s) were obtained either from BD, BioLegend or eBioscience. For surface staining cells were incubated with the respective antibodies for 20-30 minutes at 4° C. For all experiments, dead cells were excluded from the analysis using an Aqua or Near-1R Live/Dead fixable staining reagent (Invitrogen/BioLegend); doublets were excluded by FSC-Area vs. FSC-Height gating. For intracellular cytokine staining, T cells were incubated for 4-5 hours at 37° C. in RPMI containing 10% FCS with PMA (50 ng/ml), Ionomycin (500 ng/ml) and GolgiPlug (containing Brefeldin A, BD, 1:1000 dilution). After surface staining Cytofix/Cytoperm (BD) was used according to the manufacturers instructions, and Perm/Wash buffer was prepared in-house (PBS containing 0.5% Saponin and 5% BSA). For intracellular staining cells were incubated with the respective antibodies for 20-30 minutes at 4° C. For intra-nuclear FoxP3 staining, Fixation/Permeabilization buffer (eBioscience) was used after surface staining, followed by the Perm/Wash buffer prepared in-house. In general, cells were gated based on FSC-Area and SSC-Area to exclude debris, doublets were excluded by FSC-Area vs. FSC-Height gating. Dead cells were excluded from the analysis using an Aqua or Near-1R Live/Dead fixable staining reagent (Invitrogen/BioLegend). Where applicable CD45.1 cells were gated before gating on CD4 or CD8 T cells. All the markers used for gating (CD4, CD8, CD3, CD44, CD62L, CD69) show a clear separation of the negative and positive population. For the killing assay cells, singlets were gated as described above, then tumor cells were identified by Cell trace violet and an histogram showing TOPRO-3 uptake was generated. Flow cytometric analysis was carried out using either a FACSCanto II (BD) or a LSR II Fortessa (special order research product, BD and equipped with 405 nm, 488 nm, 561 nm and 640 nm laser lines) with FAGS Diva Software. Data analysis was performed using FlowJo 10.0.x (Treestar).

Flow Cytometric Analysis of STAT5 Phosphorylation

Single cell suspensions of bone marrow were surface stained for 20 minutes, after which GM-CSF containing medium (20 ng/ml) was added to the samples. Cells were incubated at 37° C. for 30 minutes to induce phosphorylation of STAT5 before addition of 4% PFA solution (pH 7.4) to a final concentration of 2%. Cells were fixed for 20 minutes, washed and resuspended in 1 ml of 4° C. methanol. After 40 minutes, cells were washed twice and resuspended in 451.11 of FAGS buffer. 5 µl of anti-pSTAT5 APC (BD Biosciences) was added to make a final staining ratio of 1:10. Cells were incubated for 45 minutes at 4° C. before a final wash step and acquisition. Flow cytometric analysis was carried out using a LSR II Fortessa (special order research product, BD and equipped with 405 nm, 488 nm, 561 nm and 640 nm laser lines) with FAGS Diva Software. Data analysis was performed using FlowJo 10.0.x (Treestar).

Phenotypic Analysis of Human PBMCs by Flow Cytometry

Cryopreserved PBMCs were stored in liquid nitrogen until thawing in a 37° C. water bath. Cells were resuspended gently in 1 ml of prewarmed cell culture medium (CCM; RPMI-1640 [PAN biotech], 10% FCS [Biochrom]), 1× I-glutamine, and 1× penicillin/streptomycin [both Life Technologies]) supplemented with 1:10,000 benzonase (Invitrogen). Cells were afterwards transferred to 5 ml tubes and washed with CCM. Cells were counted and adjusted to 20×106 cells/ml in CCM. To determine cytokine production by flow cytometry, cells were stimulated with 50 ng/ml phorbol 12-myristate 13-acetate (PMA; Sigma-Aldrich) and 1 ug/ml ionomycin (Sigma-Aldrich) in the presence of GolgiPlug (containing Brefeldin A, BD, 1:1000 dilution) and GolgiStop (containing Monensin, BD, 1:1000 dilution) for 4 h at 37° C. Nonspecific binding was blocked using Human TruStain FcX (Biolegend).

Mixed lymphocyte reaction (MLR). C57BU6 WT, Csf2$^{-/-}$, Ifng$^{-/-}$ or Il17a$^{-/-}$ responder T cells were co-cultured with DCs from BALB/c (allogeneic) or C57BU6 (syngeneic) mice. Alternatively, BALB/c WT responder T cells were co-cultured with DCs from BALB/c (syngeneic) or C57BU6 WT and Csf2rb–/– DCs (allogeneic). T cells and DCs were purified from splenocytes by positive selection using anti-CD4 and anti-CD8 (for T cells) or anti-CD11c (for DCs) magnetic beads (Miltenyi Biotec) respectively and AutoMACS Pro. Cells were plated in triplicates in U-bottom 96-well plates at a stimulator/responder ratio of 1/10 (2*10$^4$ DCs, 2*10$^5$ T cells) for 3 days in complete RPMI 1640 medium at 37° C. and 5% CO$_2$. Thereafter culture supernatants were collected and replaced by diluted 3H-thymidine (1/100, 50MCi) for 16 hours. Cells were harvested using a 96-well harvester (PerkinElmer) and scintillation was measured by a beta counter (1450 Microbeta Plus, Wallac).

Killing assays. Spleen and lymph node T cells were isolated using the Pan T Cell Isolation Kit II, mouse (MACS Miltenyi Biotec). A20-Luciferase$^+$GFP$^+$ or WEHI-3-Luciferase+ cells were stained with CellTrace™ Violet Cell Proliferation Kit (ThermoFisher Scientific, C34557). Cells were incubated at an effector/target ratio of 1:1, 20:1 and 50:1 in the presence of soluble α-CD3 (1 ug/ml) and α-CD28 (0.5 ug/ml) in RPMI supplemented with 10% FCS for 24 h at 37° C. in 5% CO$_2$. After removal of medium, Topro (0.8 µM) was added to the cells and cells were acquired on a LSRII Fortessa flow cytometer (BD). Data were analyzed using FlowJo Version X (Tree Star). The percentage specific lysis was calculated as followed: [(Experimental lysis–spontaneous lysis)/(maximum lysis–spontaneous lysis)]×100%.

Treg Suppression Assay

T cells were isolated from lymph nodes and spleen from C57BU6 WT and Csf2–/– mice, as described before. CD4 T cells were first enriched using a CD4 isolation kit (MojoSort™ Mouse CD4 Nanobeads), followed by staining with CD45, CD25, CD62L and CD4. CD4+CD25–CD62L+ (Tconv) and CD4+CD25high (Treg) cells were sorted by flow cytometry using BD FACS ARIA II cell sorter with a purity of 98-99%. APCs were irradiated with >3400 rads (4 min, 12.2 Gy/min, 225 kV, 17.7 mA) and dilute to 4×106/mL (or 2×106 cells/ml) in 10% done medium. The APCs and Tconv cells were co-cultured with autologous Treg cells at varying concentrations in a 96 well round bottom plate (4×10^4 Tconv per well). Cells were stimulated with αCD3 at a concentration of 1 ug/ml at 37° C. for 2 days and then incubated for 16 h with 3H-Thymidine. Cells were harvested using FilterMate (PerkinElmer) and analyzed by beta counter with the program Microbeta. Treg suppression percentage was calculated among living cells as [((cpm Tconv−cpm Treg:Tconv)/cpmTconv alone)*100], cpm being the counts per minute, calculated as % suppression of Tconv cells.

Cytokine analysis. Serum was obtained from allo-HCT recipient mice at the tines specified. Culture supernatants of MLR were collected after 3 days of co-culture. Measurement of GM-CSF, IFNγ and IL-17A in the serum or cell culture supernatants was performed by cytokine-specific ELISA according to the manufacturer's instructions (BD Biosciences and Biolegend).

Liver Function Parameters

Liver enzymes ((alanine aminotransferase (ALT), alkaline phosphatase (AP)), albumin and blood urea nitrogen (BUN) were measured in sera of mice using the Piccolo Liver Panel Plus (Abaxis).

Histology. For histo-pathological assessment, organs were fixed in HOPE (DCS, Hamburg, Germany) and embedded in paraffin. 3-5 µm sections were cut with a microtome (Micro HM 325, Thermo Scientific) and subsequently stained with hematoxylin and eosin. To generate the histological GvHD scores, a semi-quantitative tissue-specific scoring system was used: for the small intestine parameters including vinous blunting, crypt regeneration, crypt cell apoptosis, outright crypt destruction and lamina propria lymphocytic infiltrates were rated with the following scores: 0=normal; 0.5=focal and rare; 1=focal and mild; 2=diffuse and mild; 3=diffuse and moderate; 4=diffuse and severe, adapted from (Hill, G. R. et al. Total body irradiation and acute graft-versus-host disease: the role of gastrointestinal damage and inflammatory cytokines. *Blood* 90, 3204-3213 (1997)). For the skin the following parameters were rated: estimated hair follicle number: 0=normal (relatively closely arranged), 0.5=number slightly reduced (usually focally); estimated sebaceous glands number: 0=normal (relatively large cells, small groups, at hair neck level), 1.0=slightly reduced (number and size, usually focally), 2.0=clearly reduced (only a few cells present); sebaceous glands apoptosis & degeneration: 0=not present, 0.5=rare, 1=small number of glands involved, 2=moderate number of glands involved; hair follicle apoptosis & degeneration: 0=not present, 0.5=rare, 1=small number of follicles involved, 2=moderate number of follicles involved, 3=large number of follicles involved; leukocytic infiltration (extra-adnexal): 0=low, 1=slightly increased, 2=moderately increased; leukocytic infiltration (adnexal): 0=not present, 1=slight, 2=moderate; epidermis (apoptotic cells, leukocytic infiltration): 0=not present, 0.5=rare, 1=small number, 2=moderate number, 3=large number; subcutaneous fat: 0=continuous, 1=not continuous, 2=absent, adapted from (Kaplan, D. H. et al. Target antigens determine graft-versus-host disease phenotype. *J. Immunol.* 173, 5467-5475 (2004)). For the liver parameters including portal tract expansion and infiltrates, bile duct infiltrates, nuclear bile duct multilayering, pyknotic bile duct cells, intraepithelial bile duct cells, vascular endothelialitis, hepatocellular pan-lobular necrosis, acidophil bodies, microabscesses, mitotic figures and hepatocellular steatosis were rated with the following scores: 0=normal; 0.5=focal and rare; 1=focal and mild; 2=diffuse and mild; 3=diffuse and moderate; 4=diffuse and severe, adapted from (Hill, G. R. et al. Interleukin-11 promotes T cell polarization and prevents acute graft-versus-host disease after allogeneic bone marrow transplantation. *J. Clin. Invest.* 102, 115-123 (1998)). All slides were coded and read in a blinded fashion on an Olympus BX41TF microscope.

Human subjects. Ali human samples were collected after approval by the ethics committee of the Albert-Ludwigs University Freiburg, Germany (Protocol number: 267/11) following written informed consent. Intestinal tissue biopsies were collected in a prospective manner from individuals with GvHD or healthy controls between 2007 and 2014. Intestinal GvHD grading was performed by an experienced pathologist on the basis of histopathology according to a published staging system (Lerner, K. G. et al. Histopathology of graft-vs.-host reaction (GvHR) in human recipients of marrow from HL-A-matched sibling donors. *Transplant. Proc.* 6, 367-371 (1974)). Control individuals did not display any abnormalities in the intestinal biopsy. The patients' characteristics, including recipient age, gender, underlying diagnosis, donor and graft type, conditioning regimen, immunosuppressive regiment and GvHD grade are detailed in Supplementary tables 1 & 3 for the GvHD patients, and in Supplementary Table 2 for the control subjects.

Immunohistochemistry. Immunohistochemistry was performed in fixed paraffin-embedded tissue sections using the two-step IHC staining kit EnVision+System HRP DAKO (Glostrup, Denmark) according to the manufacturer's instructions. Sections underwent heat-mediated antigen retrieval with Dako Target Retrieval Solution (1×) for 10 min. Endogenous peroxidase activity was blocked with the DAKO endogenous peroxidase blocking kit for 30 min at RT. Primary antibodies were diluted in PBS+5% Normal Goat Serum (NGS). Single immunostaining consisted of overnight incubation at 4° C. with the unconjugated mAb anti human GM-CSF antibody (clone 3209.1; R&D Systems) or IgG isotype control for biopsies from human subjects and rat α-F4/80 (clone CI: A3-1, BioRad) and rabbit α-p22phox (clone FL-195, Santa Cruz) for mouse tissue sections. DAB was used as the chromogen. The sections were then counterstained with haematoxylin, mounted with DPX and analyzed with a light microscope Olympus BX41 coupled to a color camera ColorViwerIIIu (Olympus) and the Fiji/ImageJ software package (GNU General Public License).

Immunofluorecence

Tissues were cryosectioned (10 µm thick) for immunohistochemistry using a Hyrax C60 cryostat (Zeiss) and stored at −80° C. Sections were fixed in 4% PFA, washed in PBS, and blocked with PBS supplemented with 0.1% Triton X-100 and 4% normal goat serum. Subsequently, sections were incubated with the following primary antibodies, rat anti-GMCSF antibody (BD Pharmingen, clone BVD2-21C11, 1:50), rabbit α-CD3 (Novus, clone SP7, 1:200) and mouse anti-CD68 antibody (DAKO, Gone EMB11, 1:50), diluted in blocking solution overnight at 4° C. Sections were then washed in PBS and incubated with AF647-labeled goat anti-rat, AF488-labeled goat anti-mouse and AF555-labeled donkey anti-rabbit secondary antibodies (Life Technologies, 1:500) overnight at 4° C. or at room temperature for 1 h. Sections were mounted with SlowFade Gold antifade reagent with DAPI (Invitrogen). Fluorescence photomicrographs were captured with a SP5 Leica confocal laser scanning microscope (SP5; Leica, Heerbrug, Switzerland) equipped with argon and helium lasers using the 40× objective (oil immersion, NA1.25). Images were processed and merged by Imaris imaging software (Bitplane, Zurich, Switzerland).

TUNEL Assay

Sections fixed in 4% PFA were processed for TUNEL Assay to detect fragmented nuclei in the colon. An ApopTag Red In Situ Apoptosis Detection Kit was used according to the manufacturer's instruction. Briefly, the slides were pre-treated with H2O2 and incubated with the reaction mixture containing TdT and digoxigenin-conjugated dUTP for 1 h at 37° C. Labeled DNA was visualized with AF488-conjugated secondary antibody. Fluorescence photomicrographs were captured with a SP5 Leica confocal laser scanning microscope (SP5; Leica, Heerbrug, Switzerland) equipped with argon and helium lasers using the 40× objective (oil immersion, NA1.25). Images were processed and merged by Imaris imaging software (Bitplane, Zurich, Switzerland).

RNA isolation and quantitative rt-PCR. RNA was isolated from fixed paraffin-embedded tissue sections using the RNeasy FFPE kit (Qiagen, deparaffinization using xylene) according to manufacturer's instructions. RNA concentration was estimated using a NanoDrop 1000 spectrophotometer (Thermo Scientific). For first strand cDNA synthesis MLV reverse transcriptase (Invitrogen) was used according to manufacturer's instructions. Gene expression was measured by real-time quantitative PCR analysis using the CFX 384 Real-Time detection system (Bio-Rad, Hercules, CA, USA) with SYBR Green Supermix (Bio-Rad). Sequences for PCR primers can be found in the table below. Transcript expression was normalized to the GAPDH house-keeping gene and represented as $2^{-\Delta\Delta C_T}$ ($\Delta\Delta C_T = \Delta C_T - \Delta C_{control}$).

| Gene | Primer sequence (5' to 3') |
| --- | --- |
| CSF2 | Fwd: CAC TGC TGC TGA GAT GAA TGA AA (SEQ ID NO: 1)<br>Rev: GTC TGT AGG GAG GTC GGC TC (SEQ ID NO: 2) |
| GAPDH | Fwd: GAA GGT GAA GGT CGG AGT CAA C (SEQ ID NO: 3)<br>Rev: TGA TTT TGG AGG GAT CTC GCT C (SEQ ID NO: 4) |

Automated Population Identification in High-Dimensional Data Analysis

Data acquired in BD FACSymphony™ cell analyzer was compensated, exported in FlowJo Version v10.4 (TreeStar), normalized using Cyt MATLAB (version 2017b) and unbiased analysis were performed as described in (Nowickaet al. F1000Res 6, 748 (2017); Hartmann et al., J. Exp. Med. 213, 2621-2633 (2016).

Statistics. Graphs were prepared with GraphPad Prism (GraphPad Software). Survival curves were plotted by the Kaplan-Meier method and for comparison of survival curves a Lox-rank (Mantel-Cox) test was used. Data are displayed as individual data points or as mean+/standard deviation (SD) or standard error of the mean (SEM) as depicted in the figure legends. Comparison of the means was performed using unpaired, two-tailed Student's t-tests (with Welch correction where applicable) or one-way and two-way ANOVA with Bonferroni post-test, respectively. No statistical methods were used to predetermine sample size, but our sample sizes were similar to those generally employed in the field. No method of randomization was used.

Data availability. The datasets generated during and/or analysed during the current study are available from the corresponding authors on reasonable request.

Example 1

Figure 1B:
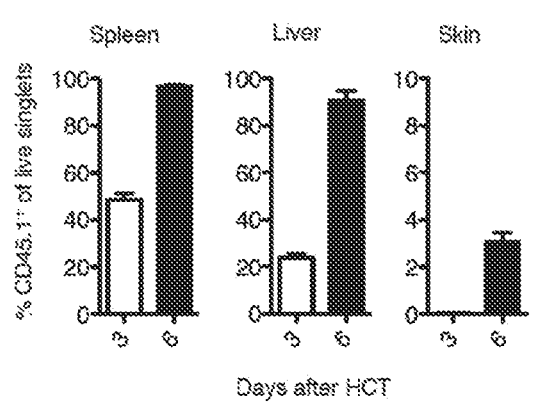
Figure 1C:
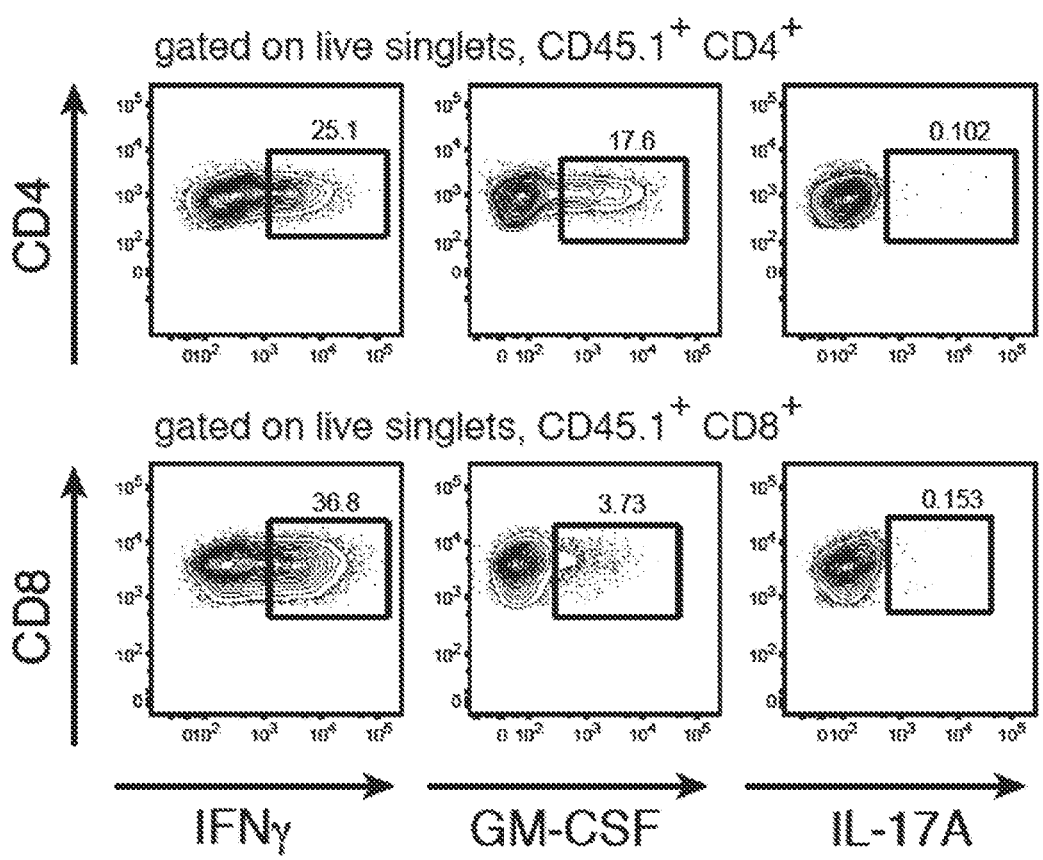
Figure 1D:
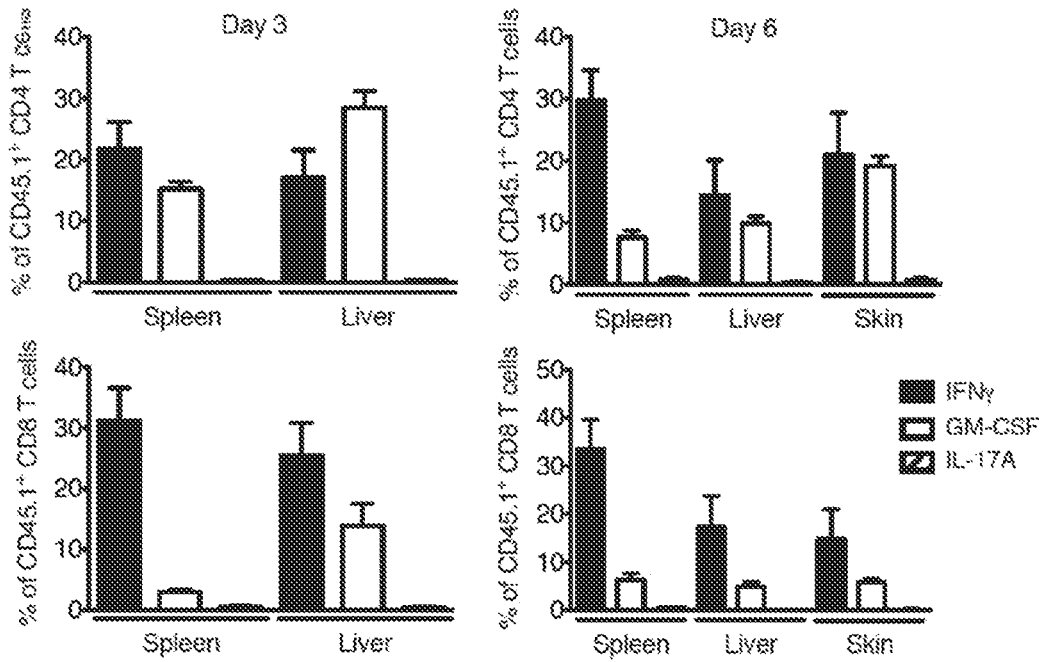
Figure 1E:
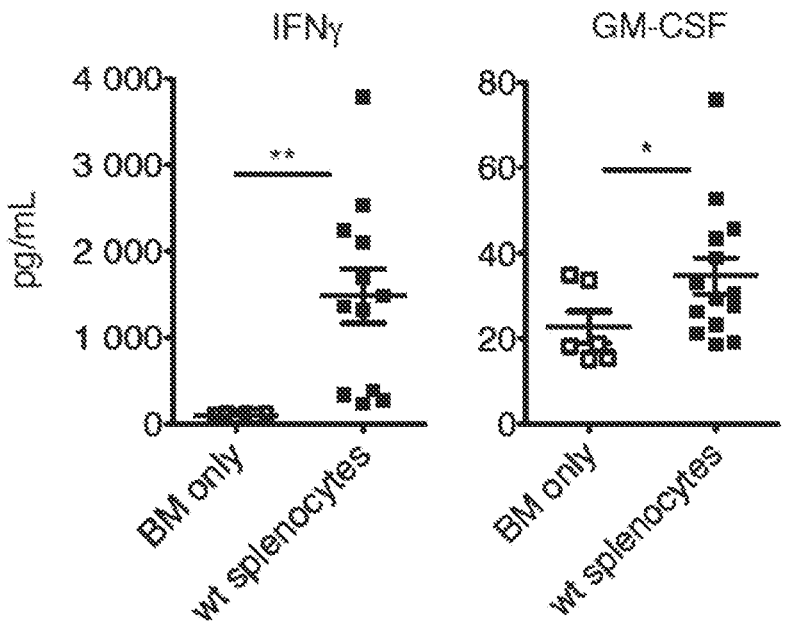
Figure 1F:
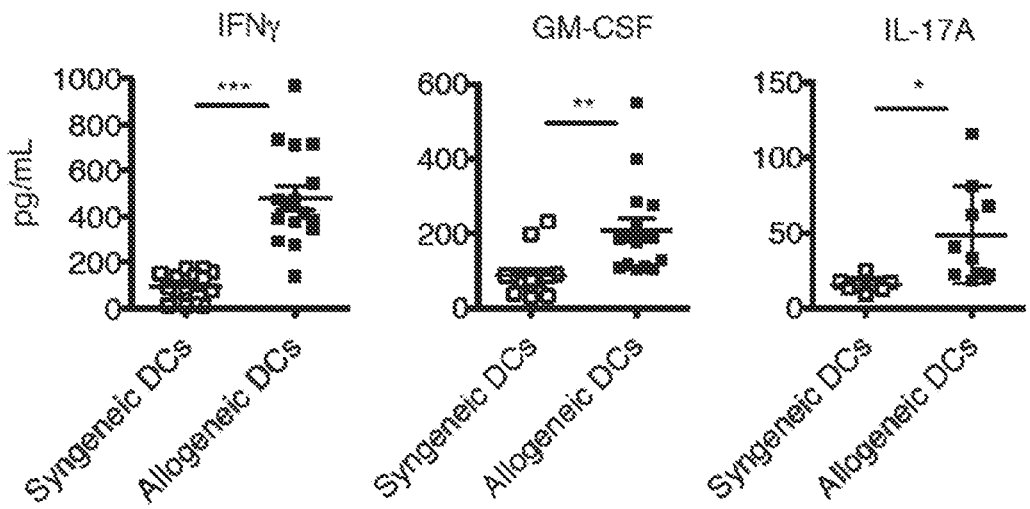
Figure 1G:
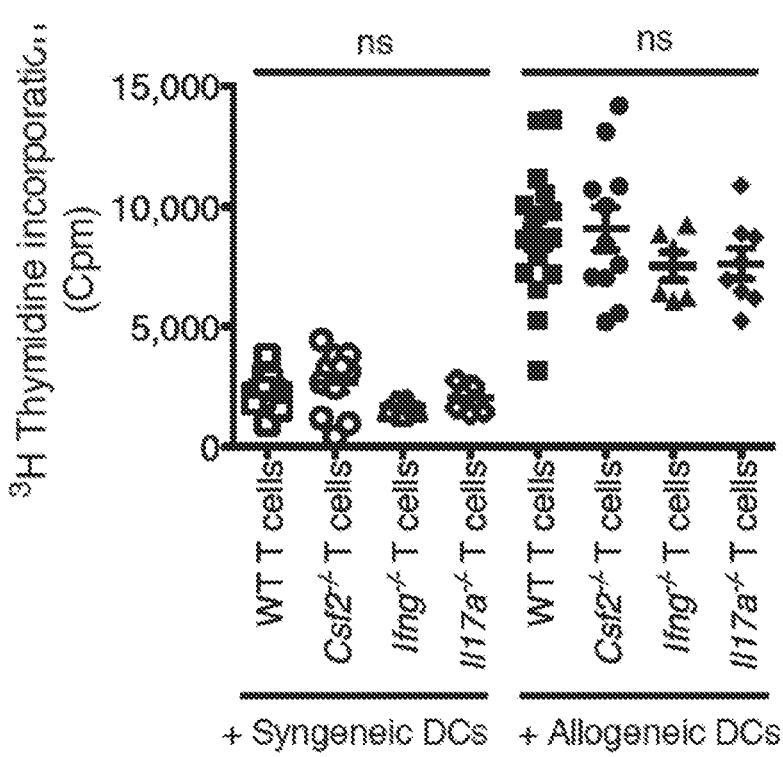
Figure 1H:
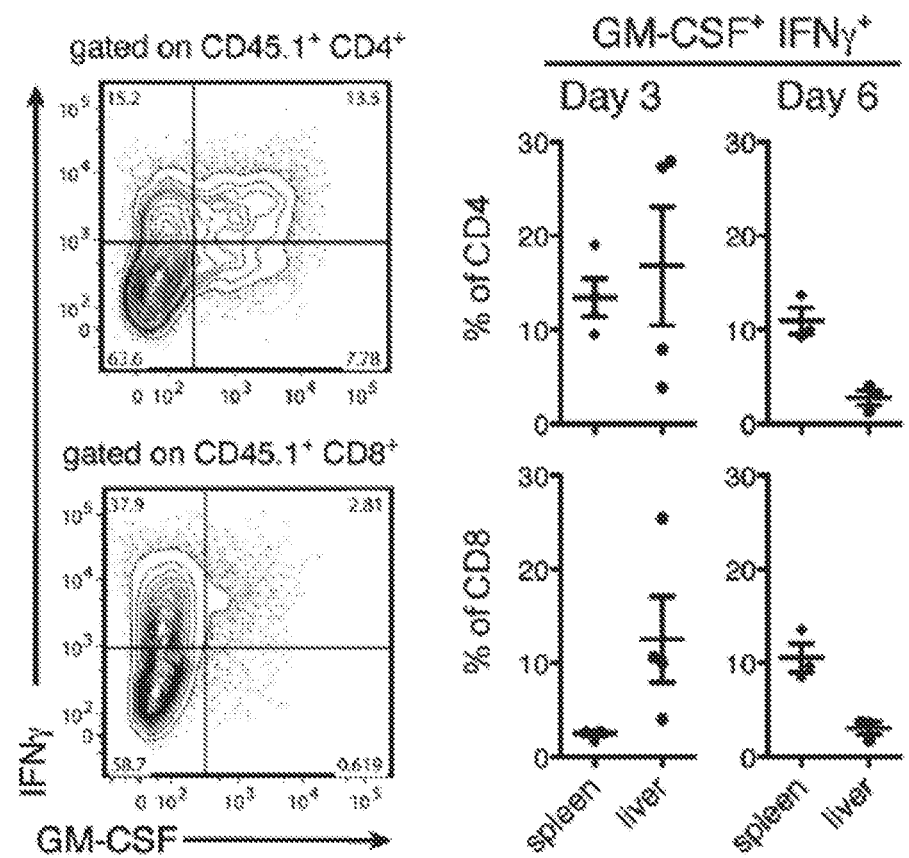

Tissue-Infiltrating Donor T Cells Produce GM-CSF and IFNγ Following MHC-Mismatched HCT To understand the contribution of T cell-derived GM-CSF to acute GvHD, the inventors first employed a model of MHC-mismatched HCT. The inventors lethally-irradiated wild-type (WT) BALB/c CD45.2$^+$ mice (MHC haplotype H2d) and then intravenously injected them with T cell-depleted (TCD) bone marrow (BM) cells from WT CD45.1 C57BL/6 (B6) mice (MHC haplotype H2b), with or without B6 CD45.1$^+$ splenocytes, which served as a source of mature T cells. Recipients of BM plus splenocytes developed fatal GvHD between days 3 and 6 after allo-HCT (FIG. 1A), which coincided with the reconstitution and expansion of donor CD45.1$^+$ cells in the spleen, liver and skin (FIG. 1B). Within the CD45.1$^+$ donor compartment, T cell populations contained high frequencies of GM-CSF- and IFNγ-producing cells, seen first in the liver (FIG. 1C) and spleen (FIG. 1D) from day 3 after allo-HCT, then in the skin from day 6 (FIG. 1D). IL-17A was barely detectable in these populations (FIGS. 1C, 1D). Accordingly, the inventors found significantly higher amounts of GM-CSF and IFNγ in sera from mice receiving BM plus splenocytes compared to BM alone (FIG. 1E). The inventors confirmed the production of GM-CSF and IFNγ during the allogeneic response in vitro using allogeneic mixed lymphocyte reactions (MLR) (FIG. 1F). Furthermore, wt, Csf2$^{-/-}$, Il17a$^{-/-}$ and Ifng$^{-/-}$ T cells proliferated equally after co-culture with allogeneic DCs, excluding a priori differences in the proliferative potential of these cells (FIG. 1G). Taken together. GM-CSF and IFNγ, but not IL-17A, are produced by T cells infiltrating target organs during GvHD.

Example 2

GM-CSF Production by Allogeneic T Cells is Essential for GvHD Pathology

Figures 2A, 2B, 2C, 2D, 2E, 2F, 2G:
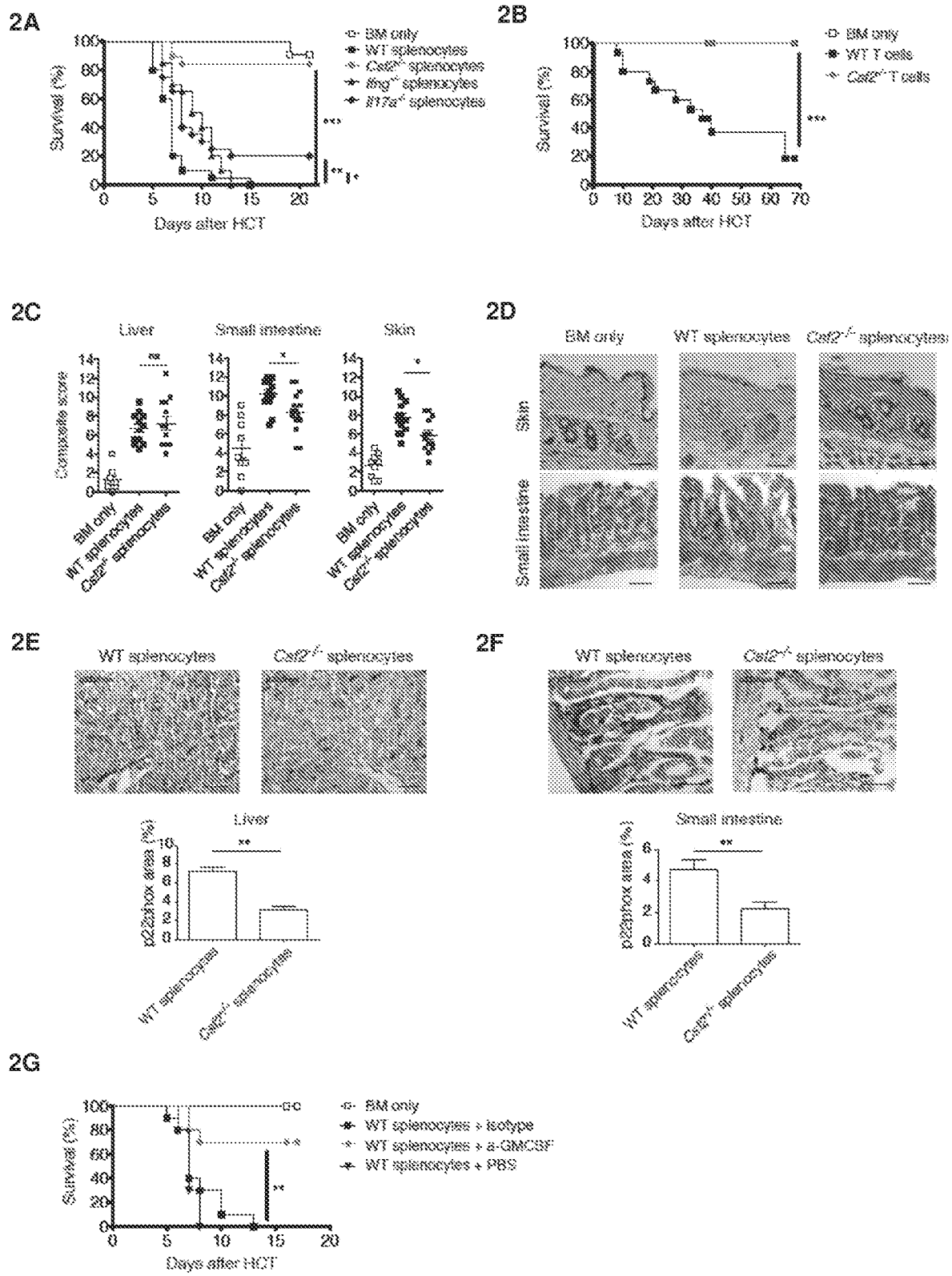

Given the production of GM-CSF and IFNγ by alto-reactive T$_H$ cells, the inventors assessed the relevance of these cytokines in determining severity of acute GvHD. As above, the inventors lethally-irradiated WT BALB/c mice and then compared the outcomes of injecting TCD-BM cells from WT B6 mice, with or without splenocytes from WT B6 mice, or from B6 mice lacking GM-CSF (Csf2$^{-/-}$), IFNγ (Ifng$^{-/-}$ or IL-17 (Il17a$^{-/-}$). Mice receiving BM plus Csf2$^{-/-}$ splenocytes were protected from lethal GvHD up to 20 days post allo-HCT, while all mice treated with BM plus WT splenocytes had died by day 15 after HCT (FIG. 2A). Injecting mice with BM plus Ifng$^{-/-}$ or Il17a$^{-/-}$ splenocytes also significantly affected the fatal GvHD kinetic, but still almost 100% of these mice died by day 20 (FIG. 2A).

Figure 6A:
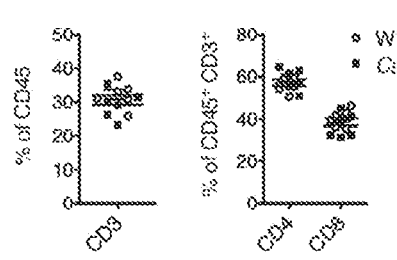
FIGS. 6A-6D Comparative phenotypic analysis of T cell populations from WT and Csf2−/− mice Flow cytometric analysis of splenic (FIG. 6A) T cell population frequencies, and (FIG. 6B) frequencies of activation marker expression in naïve C57BU6 WT and Csf2−/− mice. Data were pooled from 2 individual experiments with each n=3/group.
Figure 6B:
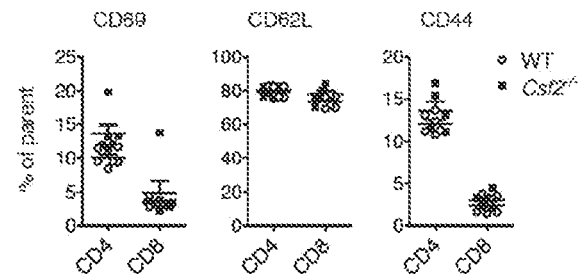
Figure 6C:
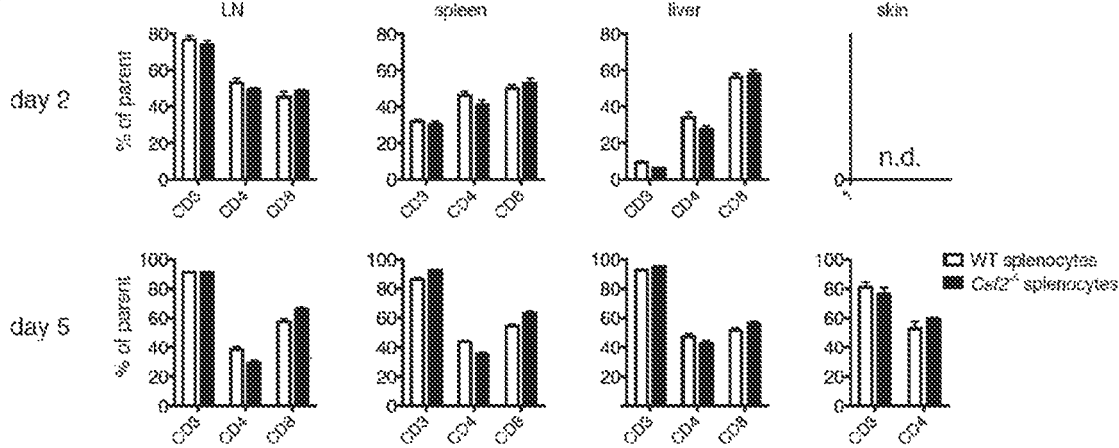
Figure 6D:
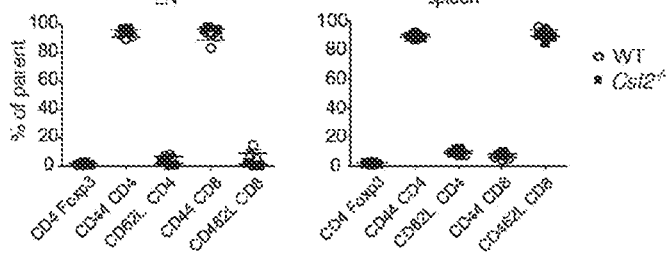

As donor splenocyte preparations contain multiple different immune cell types, the inventors then asked whether T cells were indeed the biologically-significant source of GM-CSF in our GvHD model. The inventors injected lethally-irradiated BALB/c recipients with TCD-BM cells from WT B6 donors, with or without purified T cells isolated from spleens of WT or Csf2$^{-/-}$ B6 mice; this approach confirmed that mice receiving Csf2$^{-/-}$ T cells were completely protected from lethal GvHD up to 70 days post alto-HCT, in stark contrast to those receiving WT T cells (FIG. 2B). There was no evidence that this protective effect related to innate differences between splenic T cells from WT and Csf2$^{-/-}$ mice, as the two populations exhibited comparable composition (FIG. 6A), activation status (FIG. 6B), ability to infiltrate GvHD target organs after HCT (FIG. 6C), frequencies of activated (CD44$^{high}$) T cells in spleen or peripheral lymph nodes (LN) (FIG. 6D), frequencies of regulatory T cells (Tregs) and granzyme production (data not shown) or their ability to produce proinflammatory cytokines such as IFNγ, TNFα or IL-17A. The inventors then examined the relative contribution of GM-CSF from CD4 and CD8 T cells to GvHD pathology. For this purpose, the inventors performed a "criss-cross" experiment using 4 combinations: CD4 WT T cells+CD8 WT T cells, CD4 WT T cells+CD8 Csf2-/- T cells, CD4 Csf2-/- T cells+CD8 WT T cells and CD4 Csf2-/- T cells+CD8 Csf2-/- T cells. Only the combinations in which GM-CSF was missing from the CD4 T cells conferred protection against lethal GvHD (FIG. 2K), supporting the notion that allo-reactive $T_H$ cells are a prominent source of GM-CSF in GvHD pathogenesis. Thus, the inventors conclude that T cell-derived GM-CSF is responsible for triggering lethal GvHD following MHC-mismatched HCT.

The survival advantage conferred by allo-HCT of T cells lacking GM-CSF was also evident at the level of individual GvHD target tissues. Histopathological analysis at 6 days post-allo-HCT revealed that transfer of Csf2$^{-/-}$ splenocytes caused significantly less tissue damage in skin and small intestine compared to transfer of WT splenocytes (FIG. 2C, 2D). In more detail, the skin of mice receiving Csf2-/- cells showed a decrease in cellular apoptosis and cellular infiltration around and within hair follicles and epidermis, whereas the small intestine showed a decrease in outright crypt destruction (FIG. 2D). The inventors further report here reduced colonic pathology upon Csf2-/- cell transfer, as depicted by increased colon length and a decreased apoptotic index (FIG. 2H,2I). Also, a screen for subclinical signs of liver dysfunction showed decreased serum levels of alanine aminotransferase (ALT), alkaline phosphatase (AP) and blood urea nitrogen (BUN) in mice transferred with Csf2-/- splenocytes in comparison to the WT counterparts (FIG. 2G). In addition, the systemic levels of TNFα serum levels were decreased in the absence of GMCSF, whereas the amounts of IL-6 did not change (data not shown).

As reactive oxygen species (ROS) have been implicated in GvHD tissue injury, the inventors asked whether this decreased tissue damage was associated with lower levels of ROS production. the inventors found that sections from liver and small intestine of mice 6 days post transfer of Csf2$^-$ splenocytes contained significantly fewer cells expressing p22phox, a critical component of the phagocyte ROS-production machinery, than did sections from mice receiving WT splenocytes (FIG. 2E, 2F).

To further confirm the functional role of GM-CSF in GvHD the inventors treated recipient mice with anti-GM-CSF antibodies prior to MHC-mismatched HCT of BALB/c mice with WT B6 TCD-BM alone, or with BM plus WT splenocytes. Systemically blocking the action of GM-CSF successfully replicated the survival advantage of transferring Csf2$^{-/-}$ splenocytes into these mice (FIG. 2G).

Figure 3A:
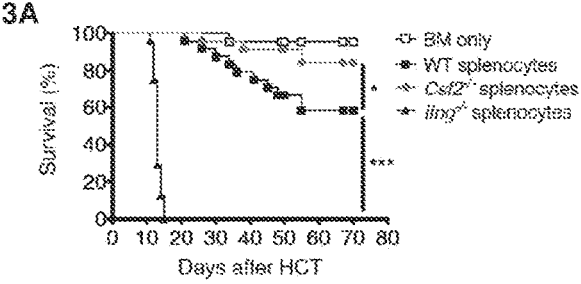
FIGS. 3A-3H GM-CSF mediates GvHD pathology following partially MHC-mismatched allo-HCT
Figure 3B:
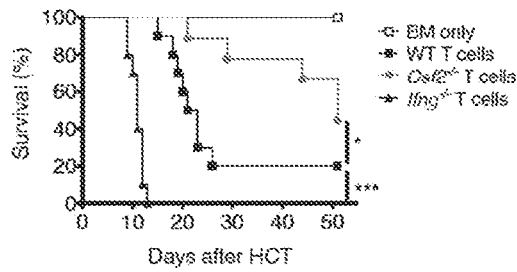
Figure 3C:
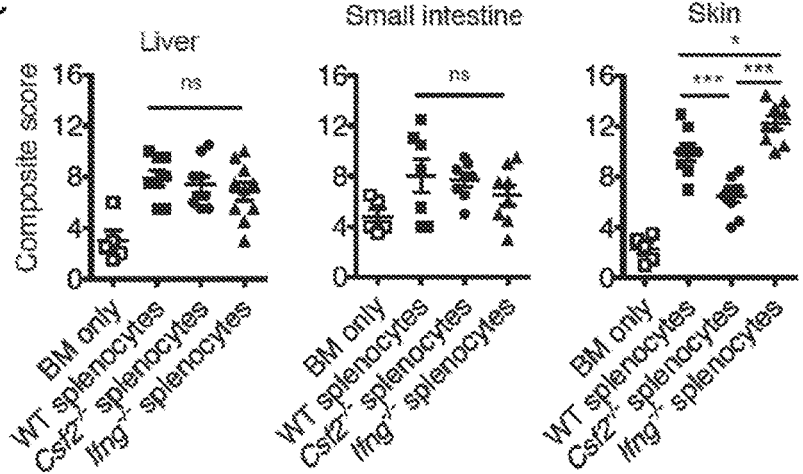
Figure 3D:
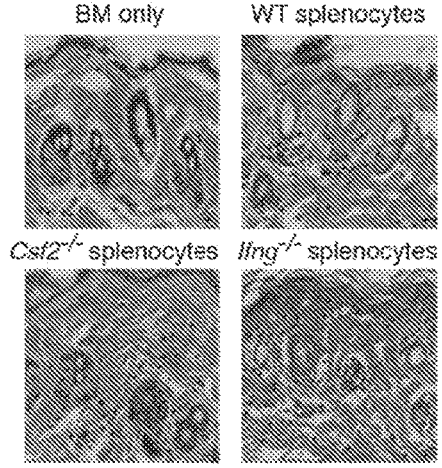
Figures 3E, 3F, 3G, 3H:
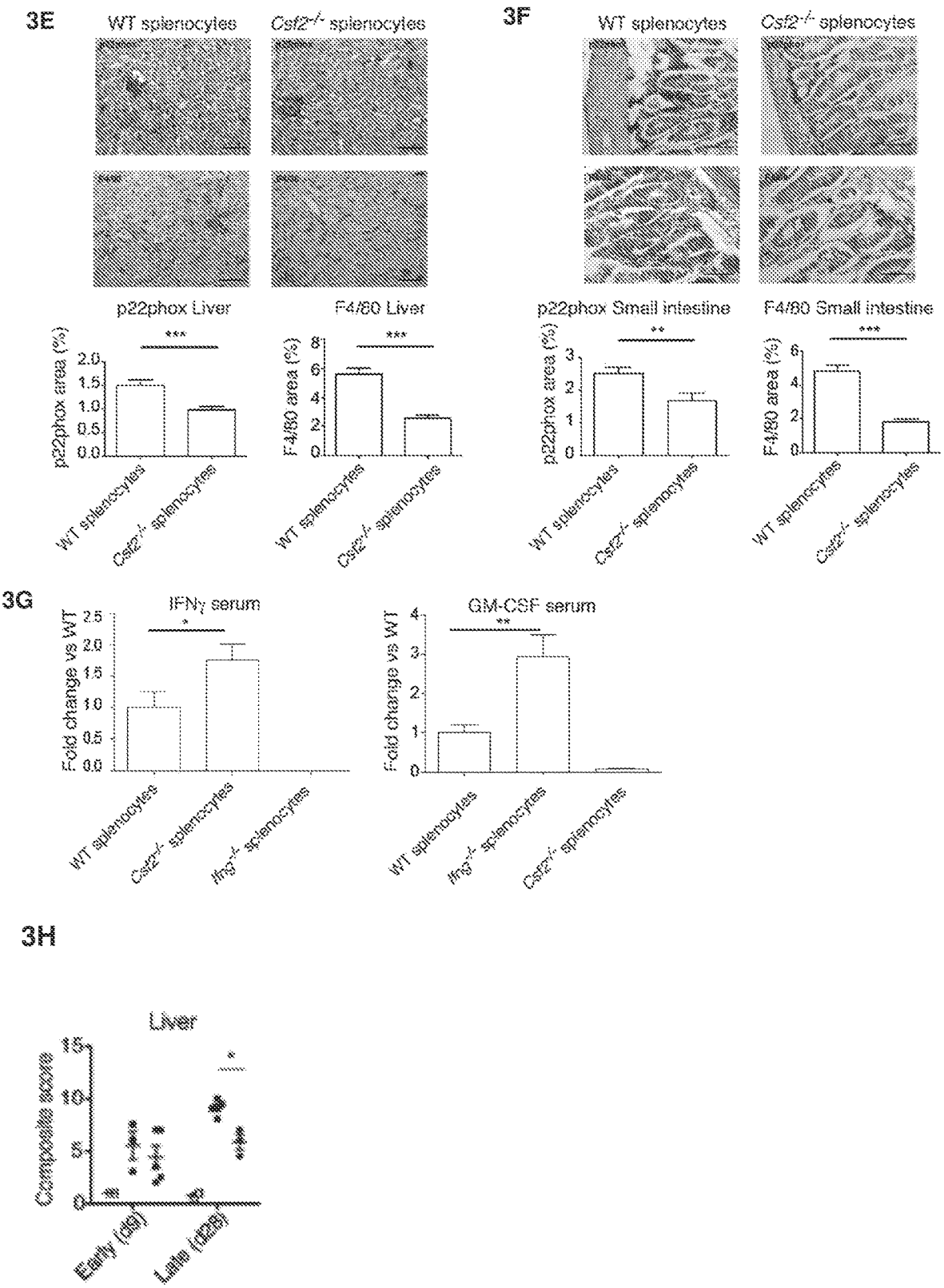

While murine models of fully MHC-mismatched HCT are informative, the inventors next asked whether the role of GM-CSF in GvHD pathology was conserved in the more clinically-relevant setting of a haplo-mismatched model of acute GvHD. The inventors combined WT B6 TCD-BM with WT, Csf2$^{-/-}$ or Ifng$^{-/-}$ splenocytes and transferred the cells into lethally-irradiated B6D2F1 mice, which are a cross between B6 and DBA mice and so bear the MHC haplotype H2b/d. Also here, the transfer of Csf2$^{-/-}$ splenocytes conferred a significant survival advantage compared to mice that received WT splenocytes, protecting mice from fatal GvHD to an almost comparable level as TCD-BM alone (FIG. 3A), which was again replicated upon the transfer of purified Csf2$^{-/-}$ splenic T cells (FIG. 3B). In both the splenocyte- and T-cell- transfer experiments, the inventors also noted a marked increase in mortality following transfer of Ifng$^{-/-}$ cells (FIG. 3A, 3B), which is consistent with the known protective, immunoregulatory function of this cytokine in GvHD. At day 9 after HCT, the skin was the most affected organ with highest histological scores; here, the inventors saw less tissue damage in mice receiving Csf2-/- compared to WT splenocytes, and more tissue damage in recipients of Ifng-/- splenocytes (FIG. 3C, 3D). This coincided with changes in sebaceous gland numbers, tissue organization and cellular infiltrates around and within hair follicles and epidermis (FIG. 3D). At a later stage (28 days) after allo-HCT, the transfer of Csf2-/- splenocytes also led to decreased liver pathology (FIG. 3H) characterized by changes in the portal tract infiltrates and bile duct disorganization. In this partial-mismatch model, the skin was the most affected organ with highest GvHD scores; here, the inventors saw significantly less tissue damage in mice receiving Csf2$^{-/-}$ compared to WT splenocytes, and significantly more tissue damage in recipients of Ifng$^{-/-}$ splenocytes (FIG. 3C, 3D). On the cellular level the inventors also observed signs of reduced GvHD in the liver and small intestine of mice receiving Csf2$^{-/-}$ cells, which had significantly fewer p22phox$^+$ cells accompanied by decreased infiltration of F4/80$^+$ myeloid cells (FIG. 3E, 3F). Given the GvHD protective role of IFNγ seen in these mice, the inventors then asked whether the absence of GM-CSF was related to levels of this cytokine: ten days after haplo-mismatch HCT, the inventors found significantly higher levels of IFNγ in mice that received csf2$^{-/-}$ splenocytes compared to WT splenocytes (FIG. 3G). Intriguingly, the inventors also uncovered evidence of increased GM-CSF in sera from mice receiving Ifng$^{-/-}$ splenocytes (FIG. 3G), suggesting that GM-CSF might additionally be mediating enhanced GvHD induced by the absence of IFNγ. Altogether, we conclude that T cell-derived GM-CSF has a vital role in the development of GvHD immunopathology in two murine models of alto-HCT.

Example 3

GM-CSF Mediates GvHD Lethality Through Donor-Derived Myeloid Cells

Figure 9A:
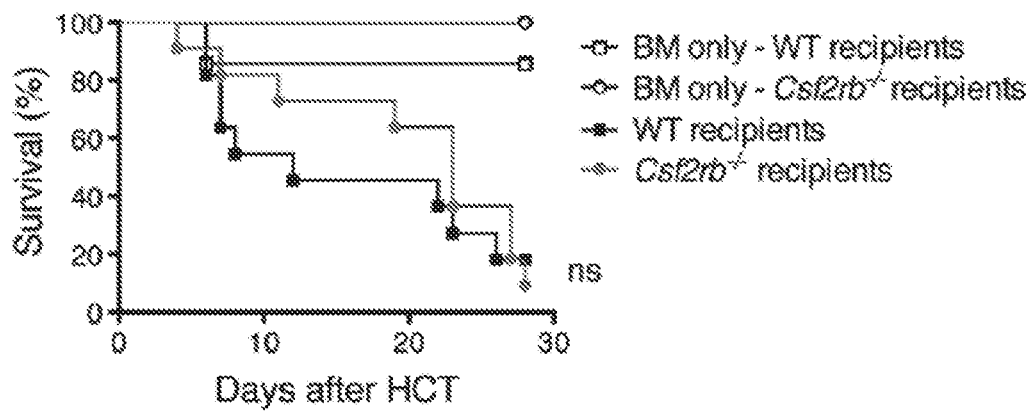
FIGS. 9A-9H GM-CSF drives GvHD through donor derived myeloid cells
Figure 9B:
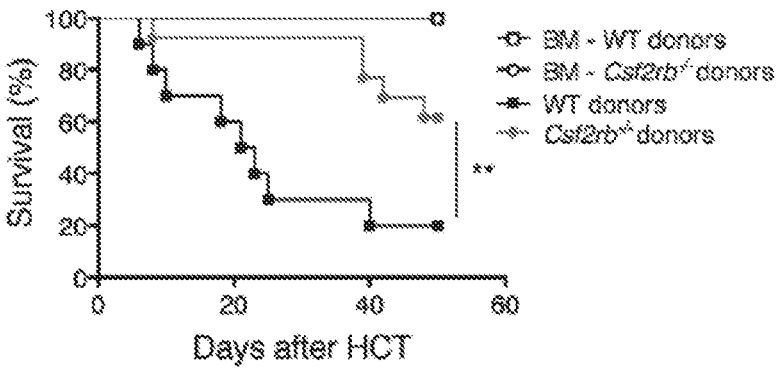
Figure 9C:
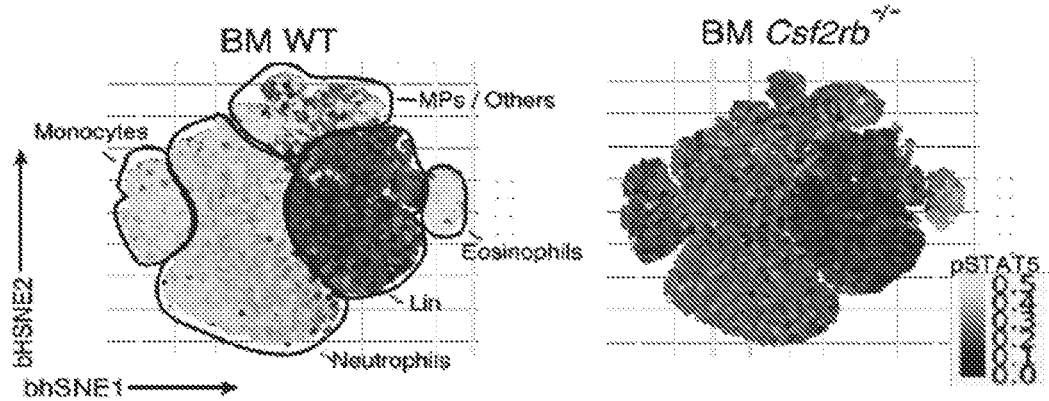
Figures 9D, 9E, 9F:
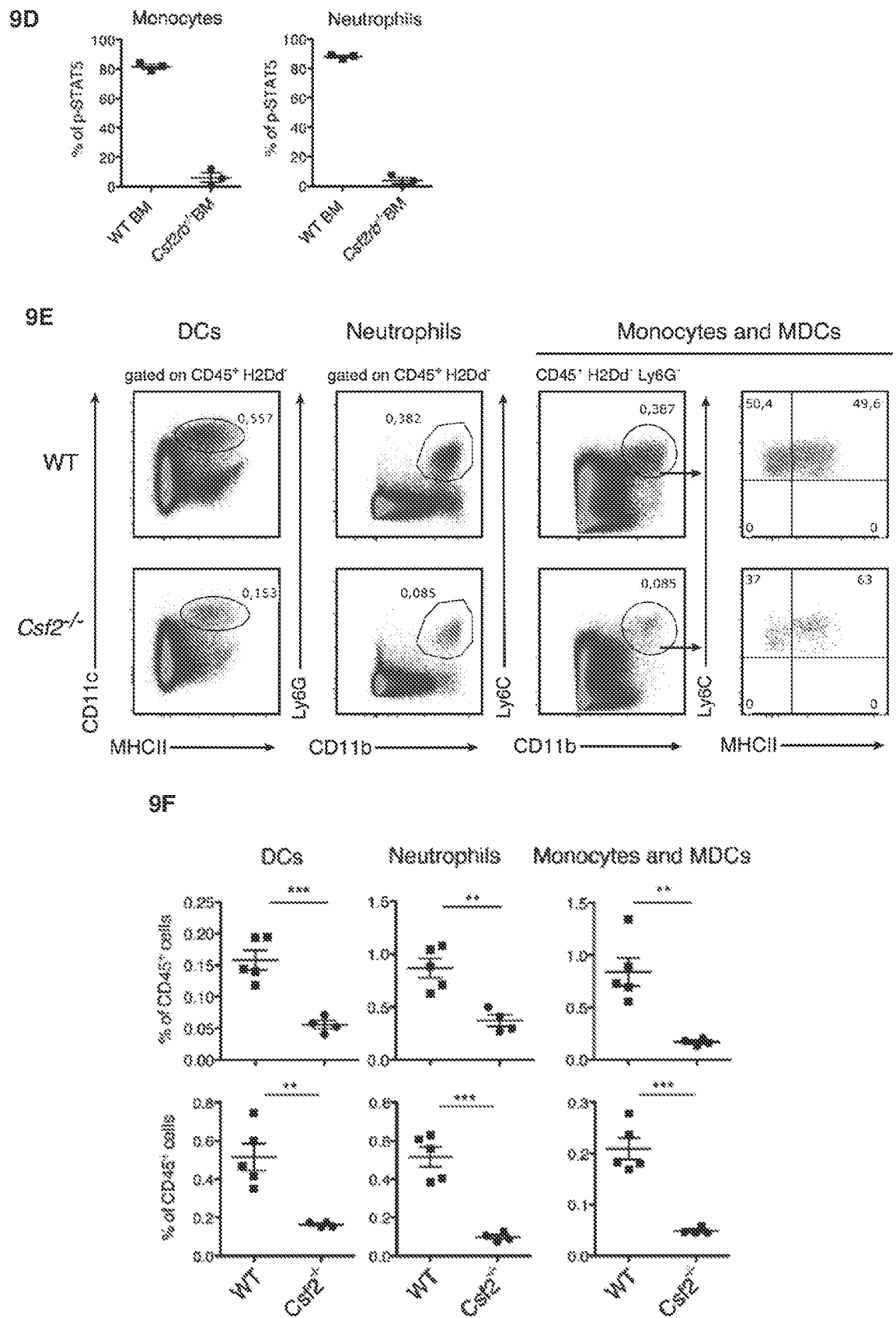
Figure 9G:
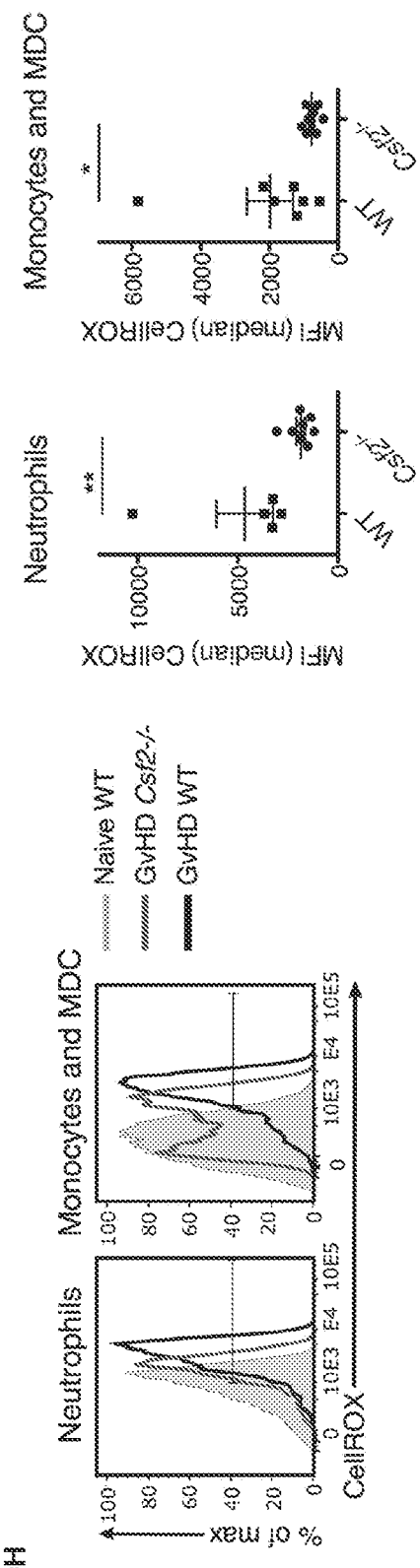
Figure 9H:
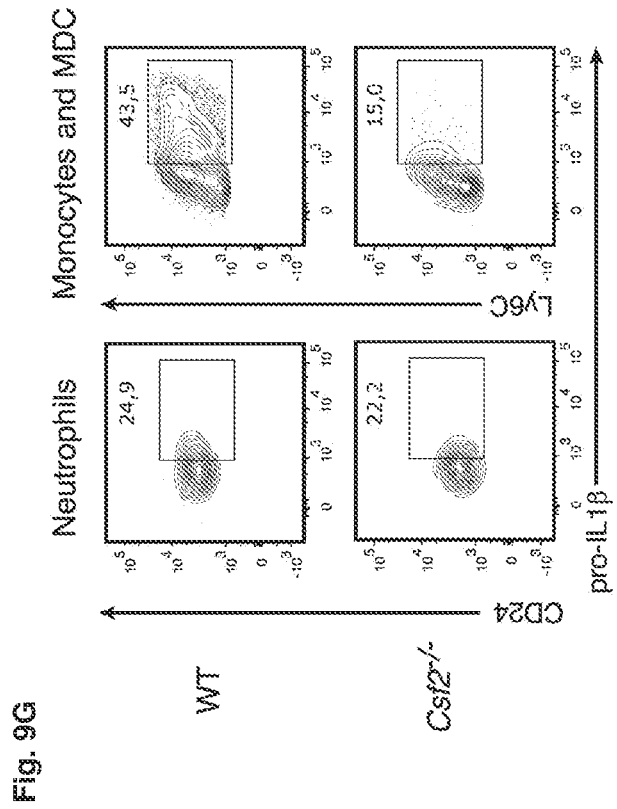

Following lethal conditioning, radio-sensitive host antigen-presenting cells (APCs) are lost within the first days after HCT and substituted by APCs from the donor. Whereas host APCs are required for the priming phase of GvHD, donor APCs play less of a role in the induction of the disease but may be involved in perpetuating tissue injury. To delineate whether the pathologically relevant GM-CSF-responsive cell type(s) are of donor or host-origin, the inventors used Csf2rb-/- mice lacking the beta subunit of the GM-CSFR as donors or hosts of HCT. GM-CSFR deficiency in the recipient compartment did not influence GvHD survival (FIG. 9A). In contrast, the transfer of BM from Csf2rb-/- mice resulted in dramatically delayed mortality (FIG. 9B), phenocopying the transfer of Csf2-/- splenocytes (FIG. 2A). The inventors used unsupervised non-linear dimensionality reduction (t-SNE) to identify and visualize the GM-CSF-responding cells within the donor graft. With this approach, the inventors found that monocytes and neutrophils were particularly sensitive to GM-CSF, which they assessed by single cell analysis of phosphorylated STAT-5, the transcription factor downstream of the GM-CSF receptor complex. Csf2rb-/- mice were used as a source of GM-CSF unresponsive cells (FIG. 9C, 9D). Having confirmed that the cells responding to GM-CSF are limited to the myeloid compartment, the inventors performed a thorough characterization of myeloid cell subsets found in the inflamed target organs 5 days after allo-HCT. The transfer of Csf2-/- splenocytes resulted in decreased frequencies of several myeloid subsets including dendritic cells (DCs), neutrophils, monocytes and monocyte-derived cells (MDCs) (FIG. 9E, 9F). A decrease in neutrophils and monocyte/MDCs was also found in target organs upon anti-GM-CSF treatment, whereas the systemic numbers of these myeloid subsets remained unaltered. The inventors observed that donor monocytes/MDCs produced less IL-16 in the absence of GM-CSF (FIG. 9G). Importantly, IL-16 is a signature cytokine of the pathogenic program elicited by GM-CSF and was shown to play a critical role in GvHD development. The inventors also investigated the expression of ROS by donor myeloid cells after alto-HCT, given their low levels in tissue sections of mice receiving allogeneic Csf2-/- T cells and their reported role in driving tissue damage. The inventors found that the transfer of Csf2-/- splenocytes led to a decreased ROS production by both the monocytes/MDCs and neutrophil subsets (FIG. 9H). Collectively, these findings demonstrate that GM-CSF-licensed donor-derived myeloid cells are crucial for GvHD pathology.

Example 4

Efficient GvL is Retained in the Absence of GM-CSF

Figure 4A:
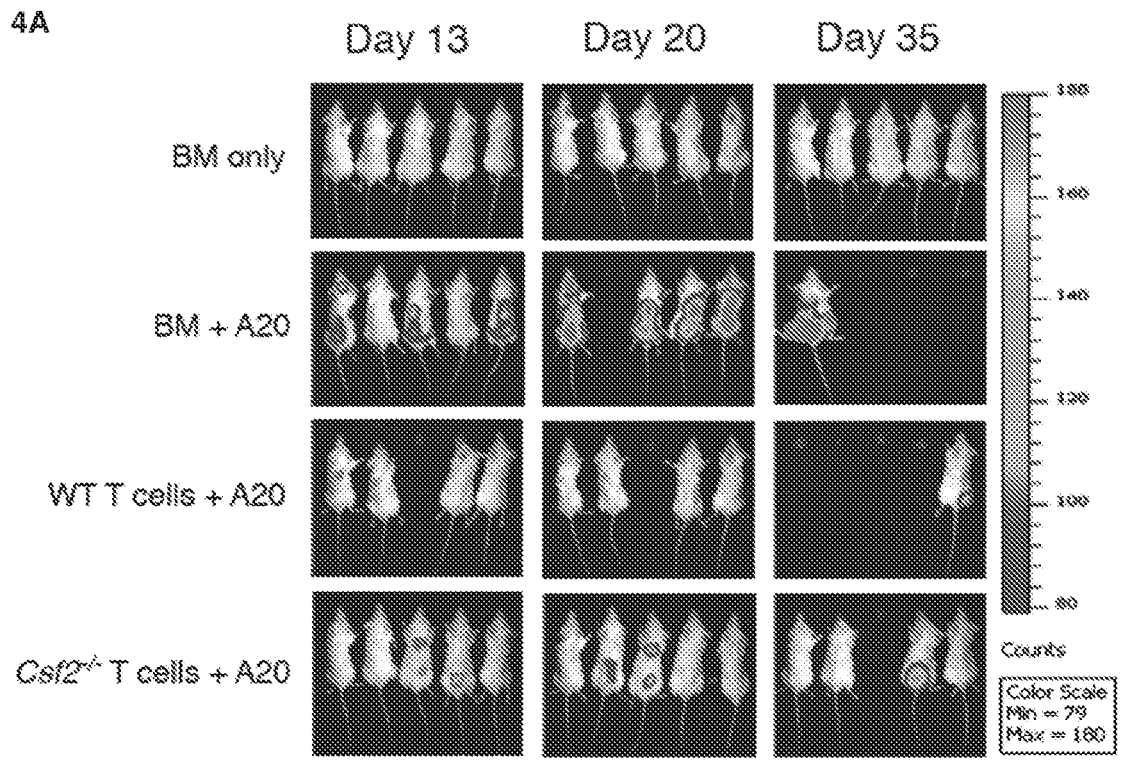
FIGS. 4A-4H GM-CSF is dispensable for anti-tumor activity following allo-HCT
Figure 4B:
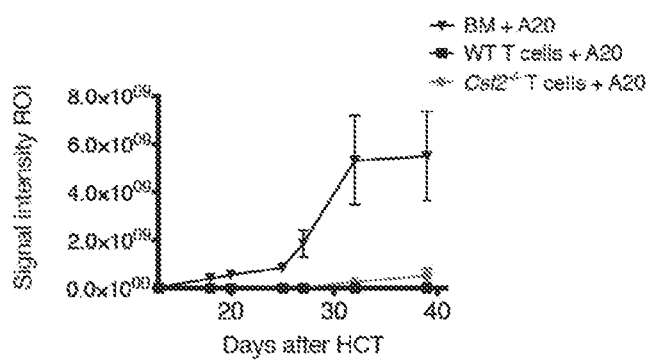
Figure 4C:
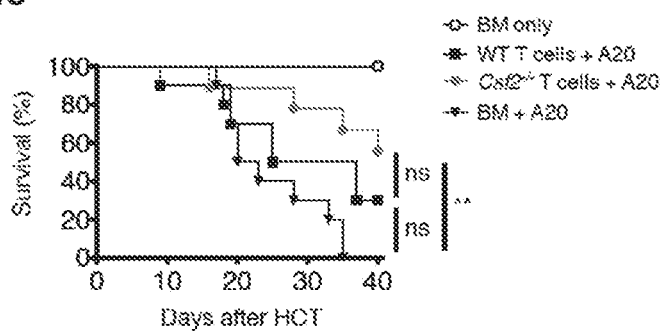
Figure 4D:
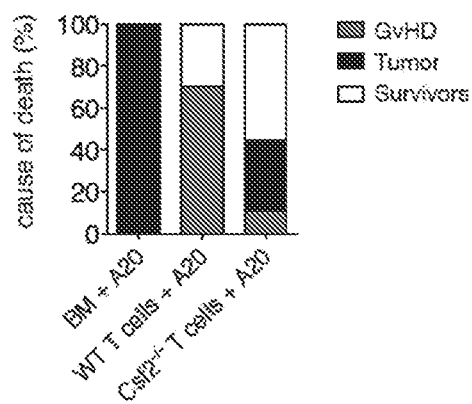
Figure 4E:
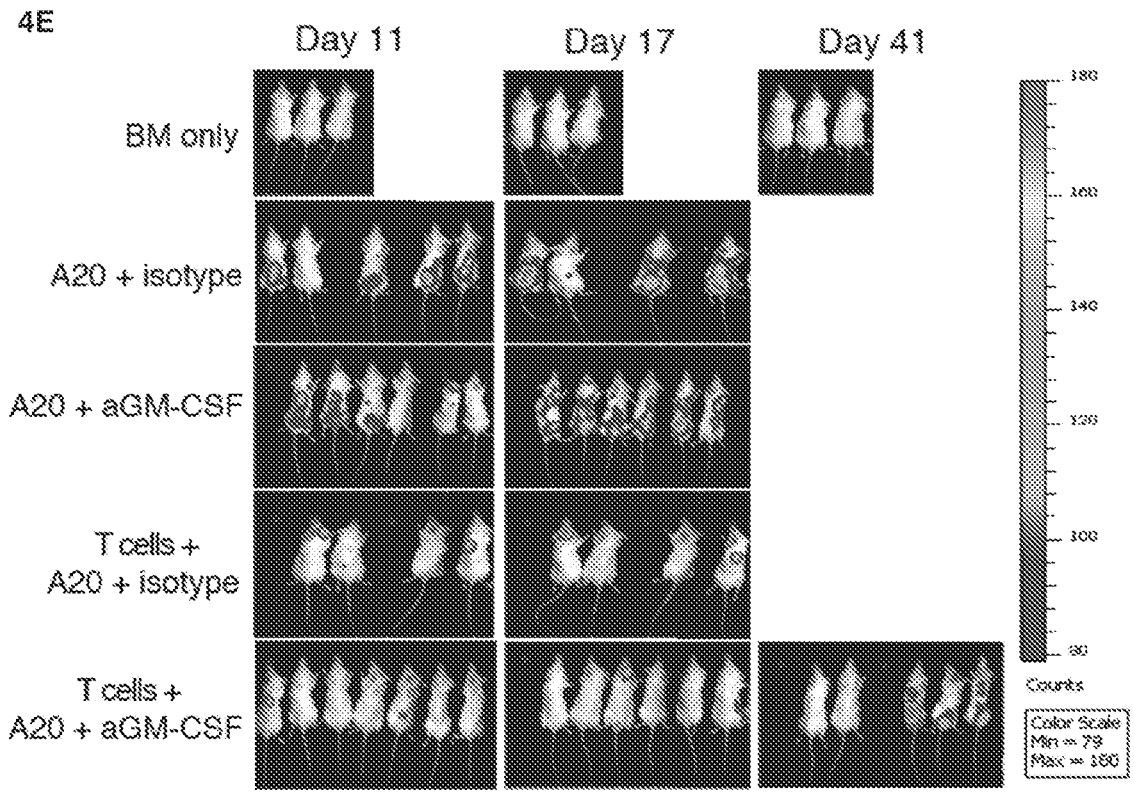
Figure 4F:
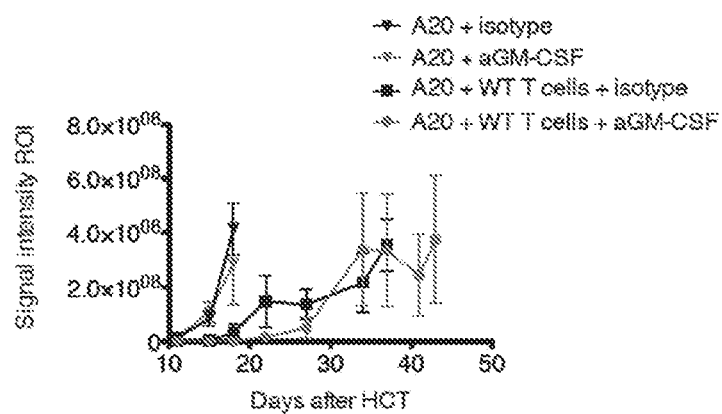
Figure 4G:
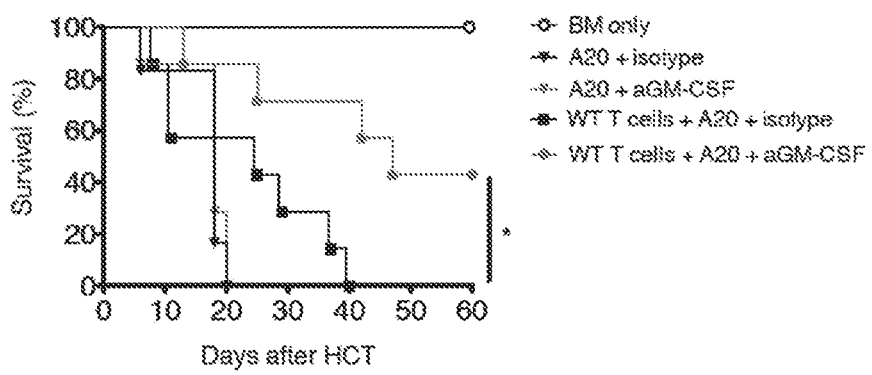
Figure 4H:
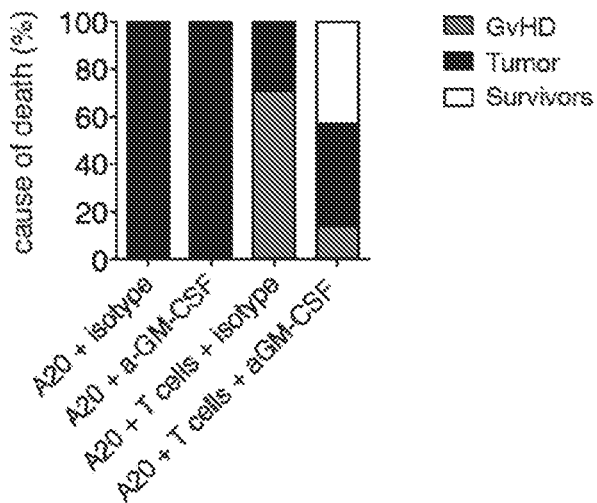

The immune responses leading to tissue damage in GvHD and tumor elimination in GvL are widely considered to be mediated through the same mechanism. As donor T cell-derived GM-CSF was essential for lethal GvHD, the inventors investigated whether it also mediated GvL in the MHC-mismatch HCT model. To test this, the inventors intravenously injected A20 B cell lymphoma cells (of BALB/c origin) co-expressing GFP and luciferase (A20-GFP-Luc) into lethally irradiated BALB/c recipients, together with WT B6 TCD-BM cells either alone or with purified B6 WT or Csf2$^{-/-}$ splenic T cells. Tumor growth was monitored by bioluminescent imaging (BLI). When A20 cells were infused with TCD-BM alone, all recipients died from the growing tumor within 35 days (FIGS. 4A-4C), consistent with a critical role for T cells in the GvL effect. Accordingly, adding WT or Csf2$^{-/-}$ T cells to the BM transfer resulted in efficient control of tumor growth (FIGS. 4A-4C), although only mice receiving Csf2$^{-/-}$ T cells showed a significant improvement in survival (FIG. 4C). Whereas lymphoma-bearing mice receiving TCD-BM plus WT T cells mainly died from severe GVHD, mice receiving TCD-BM plus Csf2-/- T cells exhibited an undiminished GvL effect, but were at the same time protected from GvHD (FIG. 4C, 4D). This improvement of survival in mice receiving Csf2-/- T cells was also observed in an alternative GvL model using the monomyelocytic cell line WEHI-3. Also, when the inventors increased the number of inoculated A20 lymphoma cells, Csf2-/- T cells executed GvL even more efficiently than WT T cells, leading to a significant increase in overall survival. Consistently, Csf2-/- and WT T cells isolated from naïve or mice receiving allo-HCT were equally capable of killing A20 lymphoma and WEHI-3 cells ex vivo, expanded equally in spleen and LN and displayed similar frequencies of activated (CD44high), proliferative (Ki67+) and granzyme B-producing cells. To test the translatability of the findings into a clinical setting the inventors used neutralizing mAbs against GM-CSF. Strikingly, anti-GM-CSF-treated leukemic mice receiving TCD-BM plus T cells showed a potent GvL effect and had significantly better survival than the isotype treated control mice (FIGS. 4E-4H). Better survival was associated with reduced GvHD incidence (FIG. 4H). Of note, neutralization of GM-CSF did not have any impact on tumor growth in mice which did not undergo HCT.

Figure 7A:
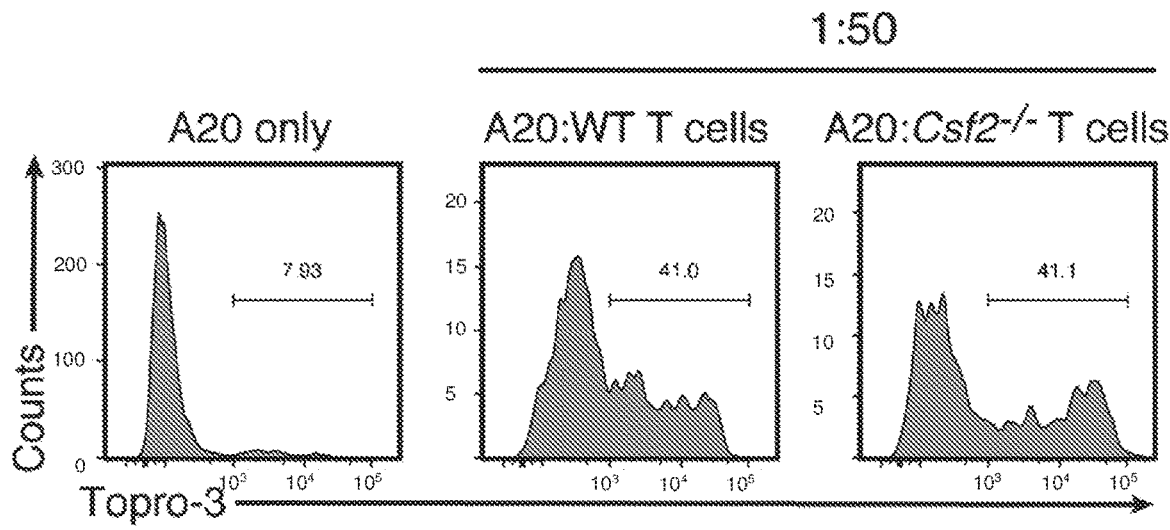
FIGS. 7A and 7B Killing assay using A20 tumor cells and T cells isolated from spleen and lymph nodes of C57BL/6 WT or Csf2−/− mice, respectively.
Figure 7B:
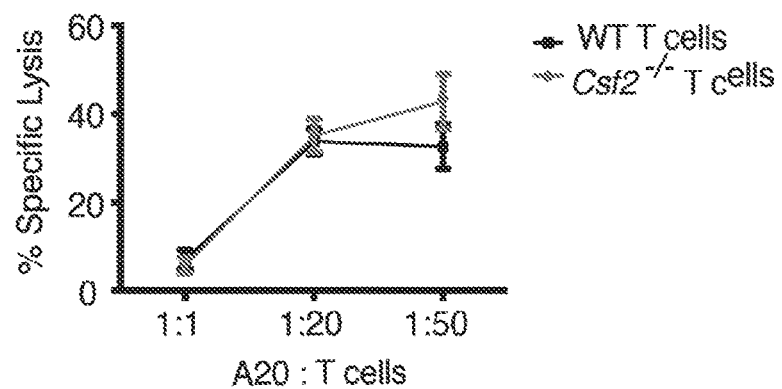

The inventors compared the cause of death (tumor or GvHD) across the different groups: Lymphoma-bearing mice which did not undergo HCT, reached the withdrawal criteria and needed to be euthanized. Lymphoma-bearing mice receiving TCD-BM plus WT T cells exhibited delayed tumor progression, but instead died from severe GVHD, whereas mice receiving TCD-BM plus Csf2$^{-/-}$ T cells exhibited a strong GvL effect, and were protected from GvHD (FIG. 4d). Consistent with these data, Csf2$^{-/-}$ and WT T cells were equally capable of killing A20 lymphoma cells ex vivo (FIGS. 7A, 7B). To test the translatability of our findings into a clinical setting the inventors used neutralizing mAbs against GM-CSF. Strikingly, anti-GM-CSF-treated leukemic mice receiving TCD-BM plus T cells showed a potent GvL effect and had significantly better survival than the isotype-treated control mice (FIGS. 4E-4H). Better survival was associated with reduced GvHD incidence (FIG. 4H). Of note, neutralization of GM-CSF did not have any impact on tumor growth in mice which did not undergo HCT.

Figures 8A, 8B:
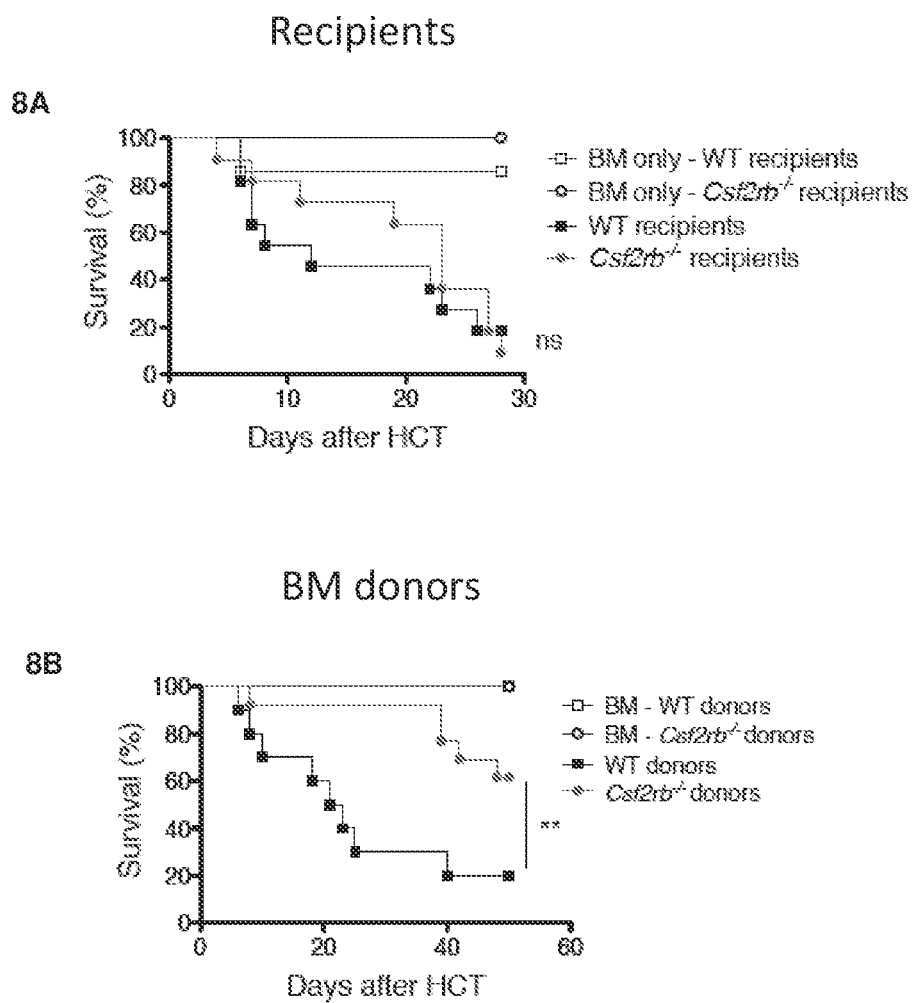
FIGS. 8A and 8B FIG. 8A: Survival of lethally-irradiated C57BU6 WT or Csf2rb−/− mice after allo-HCT with WT Balb/c T cell depleted (TCD)-BM alone or combined with splenocytes from Balb/c WT mice. Data pooled from 2 individual experiments, each with n=5-7/group.

Of note, mice receiving allo-HCT from Csfrb2$^{-/-}$ donors showed a significant improvement in survival compared to WT donors (FIGS. 8A and 8B), demonstrating that neutralization of the GM-CSF receptor is efficient in alleviating GvHD.

Thus, in the absence of GM-CSF, donor T cells are effective mediators of the therapeutic GvL response in mice, without inducing lethal GvHD, even in the highly immunogenic context of an MHC-mismatched allo-HCT.

Example 5

GM-CSF is Elevated in Human GvHD Biopsies

Figure 5A:
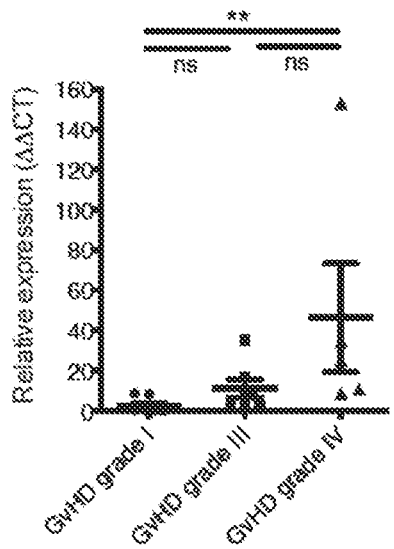
FIGS. 5A-5D Patients with severe GvHD express high levels of GM-CSF in intestinal biopsies
Figure 5B:
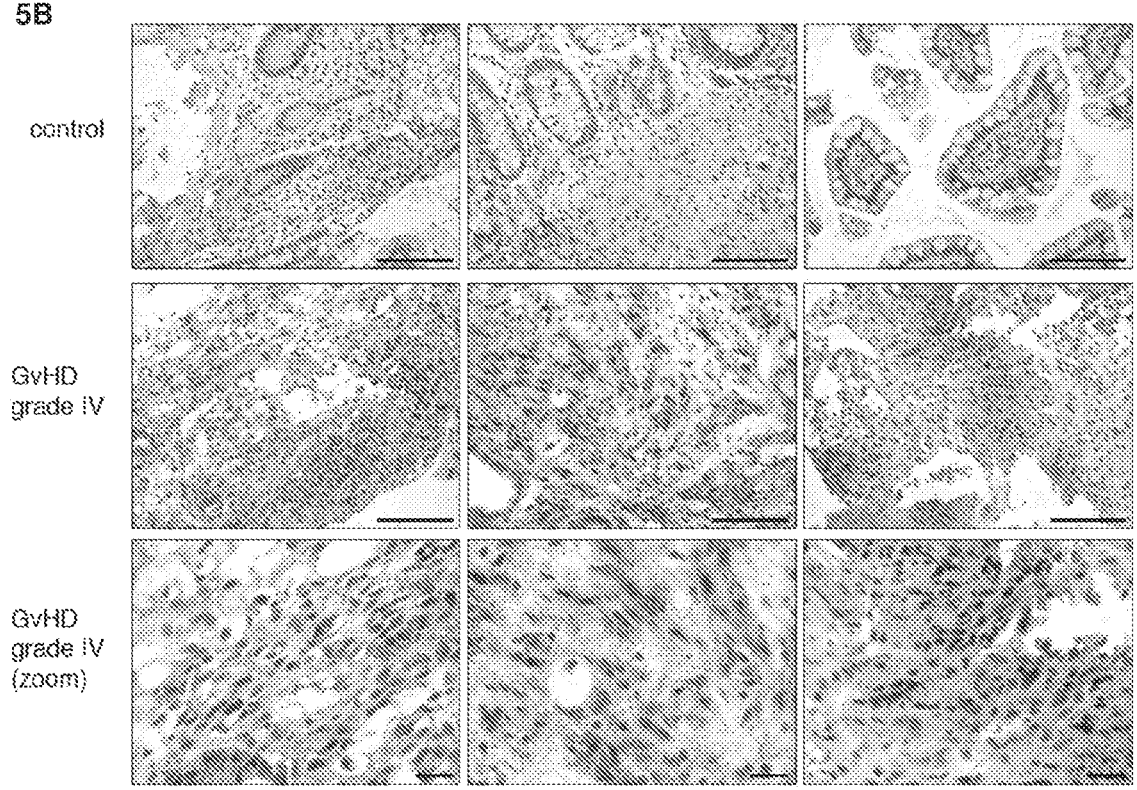
Figure 5C:
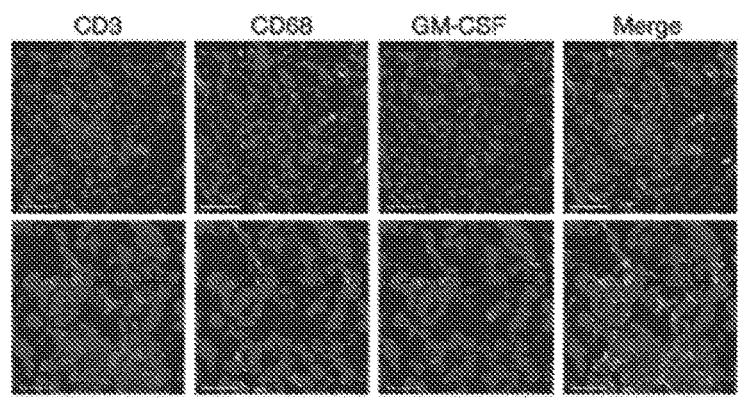
Figure 5D:
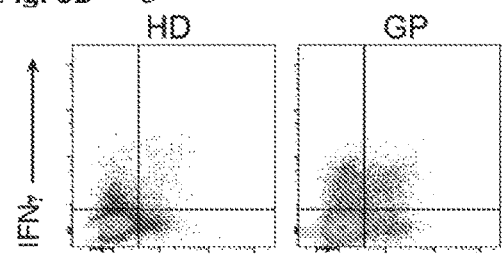
Figure 5D:
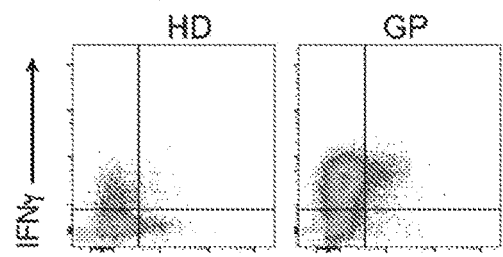
Figure 5D:
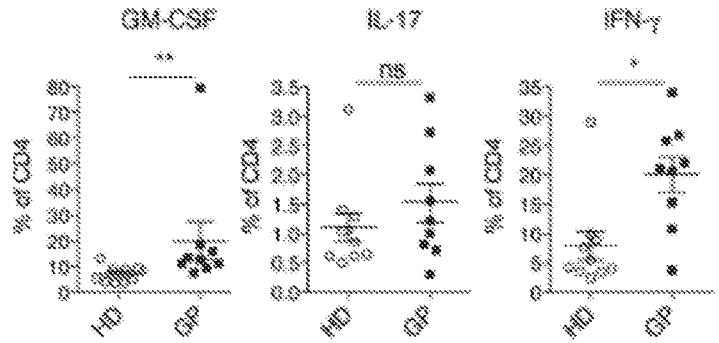
Figure 5D:
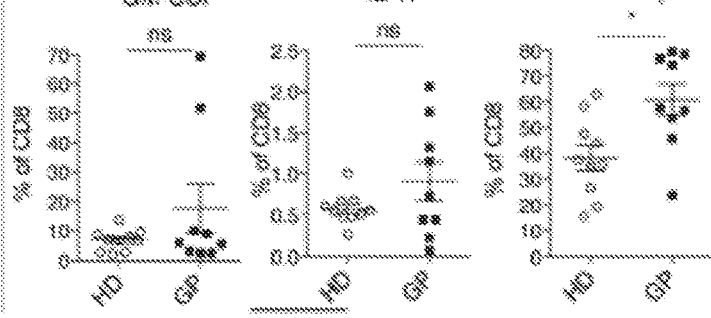

The inventors then asked whether there was evidence that GM-CSF plays a parallel role in GvHD in human HCT recipients. The inventors assessed GM-CSF gene expression and protein abundance in gastrointestinal biopsies from patients with different grades of clinically-documented GvHD following HCT for a range of different conditions (Tables 1-3). At the transcriptional level the inventors detected significantly higher expression of GM-CSF in gastrointestinal biopsies from patients with grade IV compared to grade I GvHD (FIG. 5A). Moreover, in samples from patients with grade IV GvHD, the inventors observed strong immunoreactivity for GM-CSF in the stromal compartment; while the inventors did not detect GM-CSF in biopsies from patients without GvHD (FIG. 5b). Together, these results indicate a correlation between GM-CSF and the presence of severe GvHD after allo-HCT in human patients.
Discussion:

While there is a large body of literature discussing the potential contributions of different T$_H$ cell subsets and their signature cytokines to GvHD, the mechanisms underlying inflammation and subsequent tissue destruction are not fully understood. Also, the plasticity of T$_H$ cell lineage commitment as well as the in vitro manipulation of transferred polarized T cells limits the interpretation of these results. Here, we reveal that GM-CSF plays a previously-unappreciated role in driving lethal GvHD in mice, and is similarly elevated in human allo-HCT patients with severe GvHD. Moreover, GM-CSF appears to be dispensable for the therapeutic GvL effect and so may represent a promising novel therapeutic target in GvHD prevention and treatment. Our findings also exclude a role for T-cell derived IL-17A in acute GvHD, but demonstrate a protective effect of IFNγ.

GM-CSF has been implicated in several pathological inflammatory disorders, and has potent pro-inflammatory effects on myeloid cells. Here, the inventors used two different murine models of acute GvHD to show that donor T cell-derived GM-CSF directly mediates severe GvHD, which is associated with abundant myeloid cell infiltration and increased tissue staining for components of the ROS production machinery, which is classically used by phagocytes for host defense against pathogens. The same mechanisms are clearly detrimental in the immunopathology of GvHD, where tissue damage and leukocyte infiltration go hand-in-hand. The reduction of myeloid-driven oxidative stress in GvHD-susceptible organs observed here in animals receiving allo-reactive $Csf2^{-/-}$ T cells supports this notion. The key role of GM-CSF in chronic intestinal inflammation, and the high amounts of GM-CSF found in gastrointestinal biopsies from GvHD patients suggests that modulating the amount of this cytokine in this particular organ could be highly beneficial for GvHD prevention and/or treatment.

The inventors also uncovered evidence of a potential reciprocal regulation of GM-CSF and IFNγ during GvHD in mice. IFNγ produced by activated donor T cells has previously been shown to both promote and protect against GvHD; here it was found that mice undergoing partial MHC-mismatched HCT with IFNγ-deficient splenocytes were significantly more susceptible to lethal GvHD than those receiving WT splenocytes. Intriguingly, these mice exhibited elevated levels of serum GM-CSF, while mice receiving GM-CSF-deficient splenocytes exhibited elevated IFNγ in their sera. The ability of IFNγ to negatively regulate GM-CSF in effector $T_H$ cells has been previously reported; however, GM-CSF does not directly affect T cells, which do not express the receptor complex, and thus the mechanisms by which GM-CSF influences IFNγ production will require further investigation.

There has been a long-standing assumption that donor T cell-driven GvHD and the therapeutic GvL effect are mediated via the same mechanisms: the data presented herein challenge this statement. Treating mice with GM-CSF-blocking antibodies prior to allo-HCT significantly protected from the development of lethal acute GvHD; while tumor-bearing mice treated with anti-GM-CSF benefitted from effective control of tumor growth and protection from GvHD. Thus GM-CSF does not control T cell-mediated killing of malignant lymphohematopoietic cells; instead the inventors propose, without wanting to be bound by theory, that in GvHD, GM-CSF acts as a communication conduit between pathogenic T cells and myeloid cells licensing the latter to cause tissue destruction. While GvL likely relies on direct cytotoxicity by T cells, the GM-CSF-driven responses of myeloid cells may be more relevant for GvHD pathology, thus representing a potential mechanism to separate the GvL effect from GvHD.

The pathological role of GM-CSF in autoimmune and inflammatory disorders has led to the development of monoclonal antibodies to target the GM-CSF pathway in human diseases. Given the beneficial effects of neutralizing GM-CSF in experimental GvHD seen here, it is evident that blocking GM-CSF in allo-HCT patients will improve clinical outcome. The marked increase in levels of this cytokine observed in affected tissues from severe GvHD patients further supports this idea. However, since GM-CSF is crucial for surfactant homeostasis and lung host defense, it will be important to closely monitor lung disease parameters when blocking GM-CSF in the clinical setting. There is evidence in mice that GM-CSF contributes critically to IL-23-mediated immune responses, and that anti-IL-23p19 therapy can ameliorate syngeneic GvHD-associated colitis. Thus, the direct blockade of GM-CSF might provide a valuable complement to any IL-23-targeted clinical trials. The fact that the absence of GM-CSF can halt the development of GvHD without impairing the GvL response facilitates testing this therapeutic strategy for the prevention and treatment of GvHD following allo-HCT in clinical trials. Moreover, that GM-CSF was elevated in patient samples with the severest manifestations of GvHD means that this therapeutic strategy holds particular promise for the patient groups with the poorest outcome and highest risk of fatality.

TABLE 1

Clinico-pathological features of GvHD patient set I

| Pat. Number | Gender | Age | Disease | Donor Type | Graft type | Conditioning | Immunosupp. | GvHD grade |
|---|---|---|---|---|---|---|---|---|
| 1 | Male | 44 | CVID | MRD | PBSC | FLU/BCNU/MEL | CyA/Campath | 3 |
| 2 | Male | 57 | sAML | MMURD | PBSC | FLU/BCNU/MEL | CyA/Campath/MMF | 4 |
| 3 | Female | 21 | T-ALL | MURD | PBSC | TBI/VP16 | CyA/Campath | 4 |
| 4 | Male | 69 | sAML | MURD | PBSC | FLU/BCNU/MEL | CyA/Campath | 4 |
| 5 | Male | 6 | MDS | MURD | BM | TT/FLU/ATG | CyA/MTX | 3 |

CVID: common variable immunodeficiency;
sAML: secondary acute myeloid leukemia;
T-ALL: T cell-acute lymphoid leukemia;
MDS: myelodysplastic syndrome;
MRD: matched related donor;
MMURD: mismatched unrelated donor;
MURD: matched unrelated donor;
PBSC: peripheral blood stem cells;
BM: bone marrow;
FLU: fludarabine;
BCNU: bis-chloroethylnitrosourea;
MEL: melphalane;
TBI: total body irradiation;
VP16: etoposide;
TT: thiotepa;
ATG: antithymocyte globuline;
CyA: cyclosporine A;
MMF: mycophenolate mofetil;
MTX: methotrexate.

TABLE 2

Characteristics of control subjects

| Pat. Number | Gender | Age | Biopsy |
|---|---|---|---|
| 1 | male | 59 | No pathological finding |
| 2 | male | 60 | No pathological finding |
| 3 | male | 46 | No pathological finding |

TABLE 3

Clinico-pathological features of GvHD patient set II

| Pat. Number | Gender | Age | Disease | Donor Type | Graft type | Conditioning | Immuno-suppression | GvHD grade |
|---|---|---|---|---|---|---|---|---|
| 1 | male | 70 | AML | MMURD | PBSC | FLU/BCNU/MEL | CyA, Campath | 4 |
| 2 | male | 45 | AML | MRD | PBSC | FLU/BCNU/MEL | CyA, MTX | 4 |
| 3 | male | 51 | Mantle cell lymphoma | MMURD | PBSC | FLU/BCNU/MEL | CyA, Campath | 4 |
| 4 | male | 29 | Morbus Hodgkin | haploidentical sibling | PBSC | FLU/MEL/TREOS | MMF/Cyclo-phosphamide/Everolimus | 4 |
| 5 | male | 43 | B-ALL | MURD | PBSC | TBI/VP-16 | CyA, MTX, ATG | 4 |
| 6 | male | 54 | CVID | MRD | PBSC | FLU/BCNU/MEL | CyA/Campath | 3 |
| 7 | female | 60 | MDS-RAEB II | MURD | PBSC | FLU/BCNU/MEL | CyA/Campath | 3 |
| 8 | female | 61 | AML | MMURD | PBSC | FLU/TT | CyA/Campath | 3 |
| 9 | female | 59 | T-NHL | MMURD | PBSC | FLU/TT | CyA/Campath | 3 |
| 10 | male | 76 | Acute erythroid leukemia | MURD | PBSC | FLU/BCNU/MEL | CyA/ATG/MMF | 3 |
| 11 | female | 47 | AML | MURD | PBSC | FLU/BU/TT | CyA/MMF/ATG | 3 |
| 12 | male | 52 | AML | MURD | PBSC | BU/CY | CyA/Campath | 1 |
| 13 | male | 76 | MDS-RAEB II | MURD | PBSC | FLU/BCNU/MEL | CyA/Campath | 1 |
| 14 | female | 58 | AML | MMURD | PBSC | FLU/TT | CyA/MMF/ATG | 1 |
| 15 | female | 48 | AML | MMURD | PBSC | BU/CY | CyA/MTX/MMF/ATG | 1 |
| 16 | female | 71 | sAML/MPN | MMURD | PBSC | FLU/TT/MEL | CyA/MMF/ATG | 1 |
| 17 | female | 59 | MM | MRD | PBSC | FLU/BU/TT | CyA/MMF | 1 |

AML: acute myeloid leukemia;
B-ALL: B cell-acute lymphoid leukemia;
CVID: common variable immunodeficiency,
MDS: myelodysplastic syndrome;
RAEB: refractory anemia with excess blasts;
T-NHL: T cell-non-Hodgkin lymphoma;
sAML: secondary acute myeloid leukemia;
MPN: myeloproliferative neoplasms;
MM: multiple myeloma;
MMURD: mismatched unrelated donor;
MRD: matched related donor;
MURD: matched unrelated donor;
PBSC: peripheral blood stem cells;
FLU: fludarabine;
BCNU: bis-chloroethylnitrosourea;
MEL: melphalane;
TREOS: treosulphan;
TBI: total body irradiation;
VP16: etoposide;
TT: thiotepa;
BU: busulphan;
CY: cyclophosphamide;
CyA: cyclosporine A;
MTX: methotrexate;
MMF: mycophenolate mofetil;
ATG: antithymocyte globuline.

TABLE 4

| GvHD criteria | Grade 0 | Grade 1 | Grade 2 | Grade 3 |
|---|---|---|---|---|
| Weight loss | <10% | 10-20% | 20-25% | >25% |
| Posture | Normal | Hunching noted only at rest | Moderate hunching also at movement | Severe hunching impairs movement |
| Activity | Normal | Mild to moderately decreased | Decreased | Severely decreased |
| Fur texture | Normal | Mild to moderately ruffling | Severe ruffling/poor grooming | Fur loss |
| Skin integrity | Normal | Patchy scaling of skin and/or genital oedema | Moderate scaling and inflammation of skin | Diffuse ulcerative skin lesions and severe inflammation |

We claim:

1. A method for treating a patient having a hematologic malignancy and being at risk of graft-versus-host-disease from an allogenic transplant or reducing incidence of graft-versus-host-disease in the patient having received the allogenic transplant, the method comprising:
   administering to the patient a pharmaceutical composition comprising a non-agonist ligand specifically binding to human granulocyte macrophage colony stimulating factor (hGM-CSF), wherein the non-agonist ligand specifically binding to hGM-CSF is an antibody, wherein the antibody is selected from the group consisting of namilumab, lenzilumab, and otilimab;
   treating the patient with an allogenic transplant for the hematologic malignancy;
   thereby treating the hematologic malignancy and/or reducing the incidence of the graft-versus-host-disease in the patient.

2. The method of claim 1, wherein the allogenic transplant is an allogenic hematopoietic stem cell transfer (allo-HCT).

3. The method of claim 1, wherein the ligand is a human antibody or a humanized antibody.

4. The method of claim 1, wherein pharmaceutical composition comprising the ligand is administered to the patient concurrently with or following the allogenic transplant.

5. The method of claim 1, wherein the hematologic malignancy is selected from the group consisting of leukemia, lymphoma, and a multiple myeloma.

6. The method of claim 5, wherein the leukemia is selected from the group consisting of chronic myeloid leukemia (CML), acute myelogenous leukemia (AML), chronic lymphocytic leukemia (CLL), acute lymphocytic leukemia (ALL), and acute monocytic leukemia (AMOL).

7. The method of claim 5, wherein the lymphoma is a Hodgkin lymphoma or a non-Hodgkin lymphoma.

* * * * *